(12) United States Patent
Kaminsky

(10) Patent No.: US 7,522,278 B2
(45) Date of Patent: Apr. 21, 2009

(54) REAL-TIME LINEAR-BIREFRINGENCE-DETECTING POLARIZATION MICROSCOPE

(75) Inventor: Werner Kaminsky, Seattle, WA (US)

(73) Assignee: University of Washington, Seattle, WA (US)

( * ) Notice: Subject to any disclaimer, the term of this patent is extended or adjusted under 35 U.S.C. 154(b) by 404 days.

(21) Appl. No.: 11/372,566

(22) Filed: Mar. 10, 2006

(65) Prior Publication Data

US 2007/0211333 A1    Sep. 13, 2007

(51) Int. Cl.
*G01J 4/00* (2006.01)
(52) U.S. Cl. ...................................... 356/364
(58) Field of Classification Search ................. 356/364
See application file for complete search history.

(56) References Cited

U.S. PATENT DOCUMENTS 6,924,893 B2 * 8/2005 Oldenbourg et al. ........ 356/369
7,079,247 B2   7/2006 Shribak et al.
7,220,978 B2 * 5/2007 Ma et al. ................ 250/559.45
7,233,395 B2 * 6/2007 Montarou et al. ........... 356/365

* cited by examiner

*Primary Examiner*—L. G Lauchman
(74) *Attorney, Agent, or Firm*—Olympic Patent Works PLLC

(57) ABSTRACT

Various embodiments of the present invention are directed to real-time capture, analysis, and output of polarizing microscopy images that quantify detected LB signals at discrete locations within the image. In one embodiment of the present invention, circularly polarized light is passed through a sample and optically imaged by traditional polarizing-light-microscope components. The resulting image is then split four ways and analyzed by a four-way polarizer/analyzer, and the four resulting analyzed subimages are computationally processed to produce three false-color, real-time images that represent per-pixel linear birefringence, extinction angle, and transmission at each position within a quarter-sized representation of the original image produced by conventional light-microscope imaging components. The false-color images can be produced at a rate of 30 frames per second or at greater rates by employing highly efficient image capture and computational processing of captured images through efficient programming techniques.

45 Claims, 14 Drawing Sheets

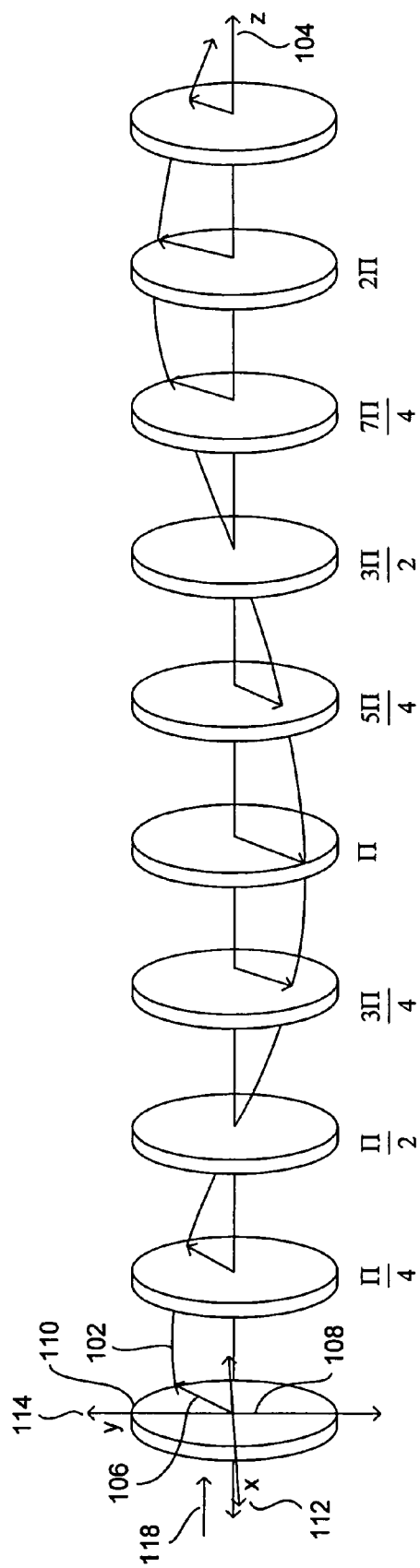
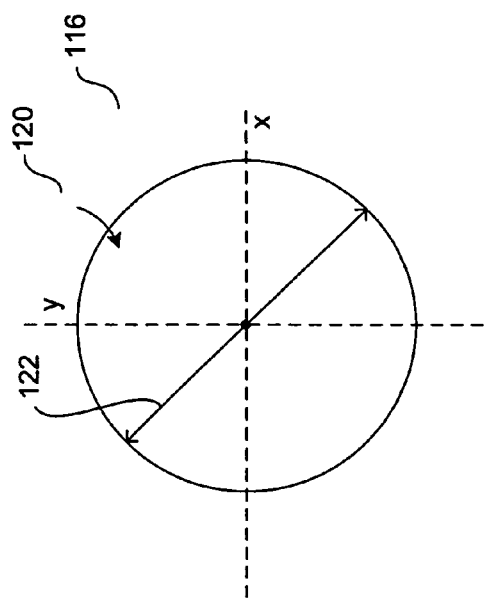

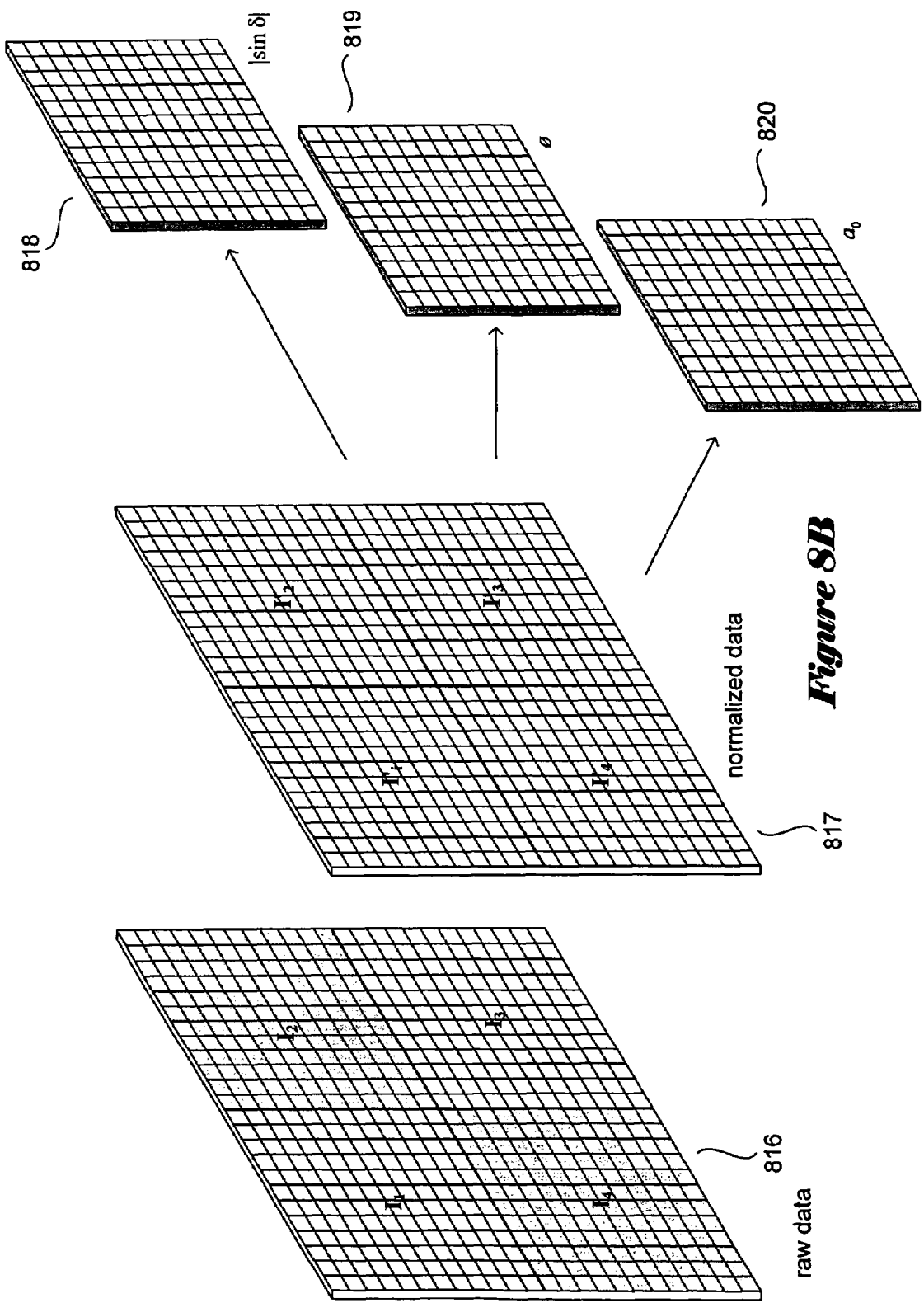

US 7,522,278 B2

REAL-TIME LINEAR-BIREFRINGENCE-DETECTING POLARIZATION MICROSCOPE

TECHNICAL FIELD

The present invention is related to detecting and displaying indications of linear birefringence in polarizing microscope images and, in particular, to an enhanced polarizing microscope that captures and processes images in real time to display representations of polarization effects resulting from anisotropic refraction of circularly polarized light by optically anisotropic samples through which circularly polarized light is passed.

BACKGROUND OF THE INVENTION

Polarizing light microscopes have been used for approximately 200 years to study, among other things, characteristics of crystalline materials and other ordered materials. More complex instruments, referred to as "circular dichroism spectrapolarimeters," are used to measure circular dichroism ("CD") in optically active materials, including proteins and other biological materials. There are four different phenomena observed when plain polarized or circularly polarized light is passed through optically active materials: (1) linear birefringence ("LB"), a phase shift between propagation modes of linearly polarized light resulting from anisotropic refraction of light by an optically anisotropic material; (2) linear dichroism ("LD"), resulting from anisotropic absorption of linearly polarized light passing through an optically active sample; (3) circular birefringence ("CB", also known as optical activity or optical rotation), resulting from a difference in refractive index of a sample with respect to left circularly polarized light and right circularly polarized light; and (4) circular dichroism ("CD"), resulting from differential absorption of left circularly polarized light and right circularly polarized light by an optically active sample. Often, two or more of these phenomena are convolved in light propagating through various media, producing complex observed effects that were formerly difficult to analyze. During the past 50 years, relatively straightforward mathematical descriptions of these polarization-related phenomena have been developed and have allowed for development of instruments and computational methods for detecting, deconvolving, and quantifying LB, LD, CB, and CD signals in a variety of instruments in which polarized light is passed through samples. As one example, Metripol® produces a polarizing-light-microscope system for detecting LB.

Detection and quantification of LB, LD, CB, and CD signals can provide useful information in a wide variety of different applications. For example, CD signals generated from protein samples are related to the presence of optically active secondary and tertiary structure within the protein samples, and provide a means for characterizing dynamic conformational changes within a protein sample. Polarization effects in biological samples may be used for image-contrast purposes as well as for detecting dynamically changing macromolecular structures and polymer orientations related to a wide variety of different biological effects and phenomena. In one recently recognized application, real-time detection of LB signals in sample wells in which crystals are grown provides the basis for automated crystal detection and may facilitate massive crystallization efforts needed for high-volume and high-throughput molecular structure determination by x-ray crystallography that is a cornerstone of current efforts in proteomics, structural genomics, and structural biology.

Unfortunately, current polarizing microscopy techniques rely on relatively complex hardware involving mechanical rotation of samples and/or polarizers as well as on relatively intensive computational analysis of multiple captured images in order to produce a final image that indicates the presence or absence of an LB signal at discrete locations within the image. These methods are currently too slow, cumbersome, and expensive for use in automated detection of crystals, real-time biological-sample imaging, and many other uses. Researchers, developers, and equipment vendors have thus recognized the need for a real-time imaging system that reveals and quantifies LB signals within images collected by polarizing microscopy and other techniques.

SUMMARY OF THE INVENTION

Various embodiments of the present invention are directed to real-time capture, analysis, and output of polarizing microscopy images that quantify detected LB signals at discrete locations within the image. In one embodiment of the present invention, circularly polarized light is passed through a sample and optically imaged by traditional polarizing-light-microscope components. The resulting image is then split four ways and analyzed by a four-way polarizer/analyzer, and the four resulting analyzed subimages are computationally processed to produce three false-color, real-time images that represent per-pixel linear birefringence, extinction angle, and transmission at each position within a quarter-sized representation of the original image produced by conventional light-microscope imaging components. The false-color images can be produced at a rate of 30 frames per second or at greater rates by employing highly efficient image capture and computational processing of captured images through efficient programming techniques. Additional embodiments of the present invention may include additional processing of the optical image and false-color images in order to identify and characterize optically active regions of an image and may be directed to producing false-color images representative of other quantified polarization phenomena. In still additional embodiments of the present invention, polarization effects in a variety of different optical images generated from lenses and other imaging systems can be detected and displayed by multi-way multiplexing and analyzing the images and computing polarization effects using method embodiments of the present invention.

BRIEF DESCRIPTION OF THE DRAWINGS

FIGS. 1A-B illustrate a simple, plain-polarized light wave and a z-axis projection of the path of the electric vector of the plain-polarized light wave.

FIGS. 8A-B illustrate capture and computational processing of the four-way multiplexed and four-way analyzed image by a processing component the LB-microscope system that represents one embodiment of the present invention.

DETAILED DESCRIPTION OF THE INVENTION

Figure 2A:
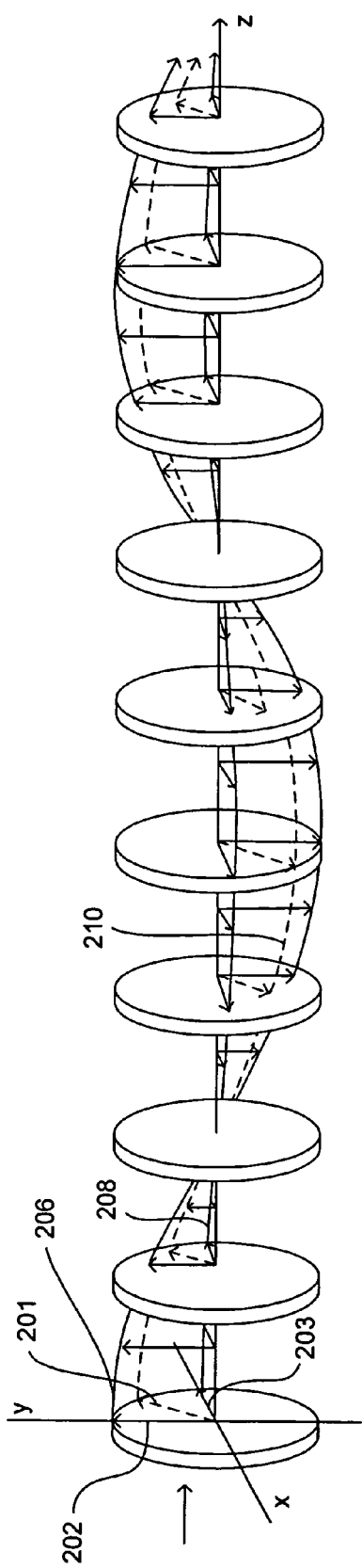
FIGS. 2A-B illustrate resolution of the plain-polarized light wave illustrated in FIGS. 1A-B into two, orthogonal, in-phase light waves.

Embodiments of the present invention are directed to real-time imaging of samples by polarizing light microscopy, computation of the linear birefringence ("LB") signal at each point in the optical image, and real-time generation and display of computed images that show the computed linear birefringence, the computed extinction angle, and the computed transmission at each point in the original, polarizing-light-microscope-generated image. In a first subsection, below, a brief overview of polarized light is provided. In a second subsection, an enhanced polarizing, optical microscope that represents one embodiment of the present invention is discussed. In a third subsection, an image-analysis software program that represents one embodiment of the present invention and that generates false-color images representing linear birefringence, extinction angle, and transmission at each point in the optical image is discussed.

Polarized Light

FIGS. 1A-B illustrate a simple, plain-polarized light wave and a z-axis projection of the path of the electric vector of the plain-polarized light wave. FIGS. 1A-B employ illustration conventions used subsequently in FIGS. 2A-B, 3A-C, and 4A-C. In FIG. 1A, a plain-polarized light wave 102 is shown plotted with respect to a three-dimensional Cartesian coordinate system. The light wave 102 travels in the z direction represented by the z axis 104. Although a light, as any electromagnetic disturbance, comprises orthogonally disposed electric-field and magnetic-field oscillations, represented by orthogonal electric and magnetic vectors, only the electric vectors are illustrated and discussed. At each instance in time, the electric vector that characterizes the real, or electrical, portion of the light wave points from a position on the z axis to the light wave, or, in other words, described a point on the light wave corresponding to a position on the z axis. For example, electric vector 106 represents the position of the light wave at an arbitrary zero point 108 in space or time. The electric vector resides in an x/y plane normal to the z axis and coincident with the zero point 108. This x/y plane is represented in FIG. 1A by a disk 110. Disk-like representations of the x/y plane at various points along the z axis are shown in FIG. 1A in order to show the magnitude and direction of the electric vector at various positions along the z axis. In FIG. 1A, and in subsequent figures, the disk-like representations of the x/y planes are shown at regular intervals of $$\frac{\pi}{4}$$

radians, with $2\pi$ radians representing a single, complete oscillation of the light wave. The z axis can be viewed as a spatial axis, with the entire plotted wave 102 representing the plane-polarized wave at an instance in time in three-dimensional space, or may be viewed as a time axis, representing the magnitude and direction of the electric vector of the light wave at a particular point in three-dimensional space at different instants in time.

In the plain-polarized light wave shown in FIG. 1A, the electric vectors at each point in space, or at each point in time, lie within a single plane parallel to the z axis and oriented at an angle of 45°, or $$\frac{\pi}{4}$$

radians, with respect to the x and y axes 112 and 114, respectively. Projecting the motion of the electric vector at each point in time or space along the z axis results in the z-axis projection 116 shown in FIG. 1B. This projection represents a view down the z axis from behind the disks in FIG. 1A, as indicated by arrows 118 and 120. When viewed in a z projection, the electric vector oscillates along the diagonal line 122.

Figure 2B:
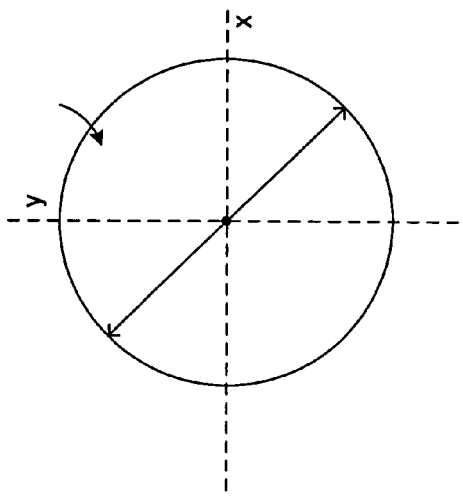

FIGS. 2A-B illustrate resolution of the plain-polarized light wave illustrated in FIGS. 1A-B into two, orthogonal, in-phase light waves. As shown in FIG. 2A, the electric vector for the plain-polarized light wave shown in FIG. 1A, such as electric vector 201, can be resolved into a vector 202 parallel to the y axis and a vector 203 parallel to the x axis. The y-axis electric-vector components describe a y-axis component wave 206 that is plain polarized in the y direction, and the x-axis components describe an x-axis component light wave 208 that is plain-polarized in the x direction. Vector combination of the two component light waves produces the plain-polarized light wave 210 illustrated in FIG. 1A and shown by a dashed line in FIG. 2A. Thus, any plain-polarized light wave, regardless of the orientation of the plane of the light wave in an arbitrary x/y plane, can be viewed as the vector combination of two, orthogonal light waves parallel to the x and y axes. The z-axis projection of the plain-polarized light wave represented by x-axis-component and y-axis-component light waves remains unchanged, as shown in FIG. 2B.

Figure 3A:
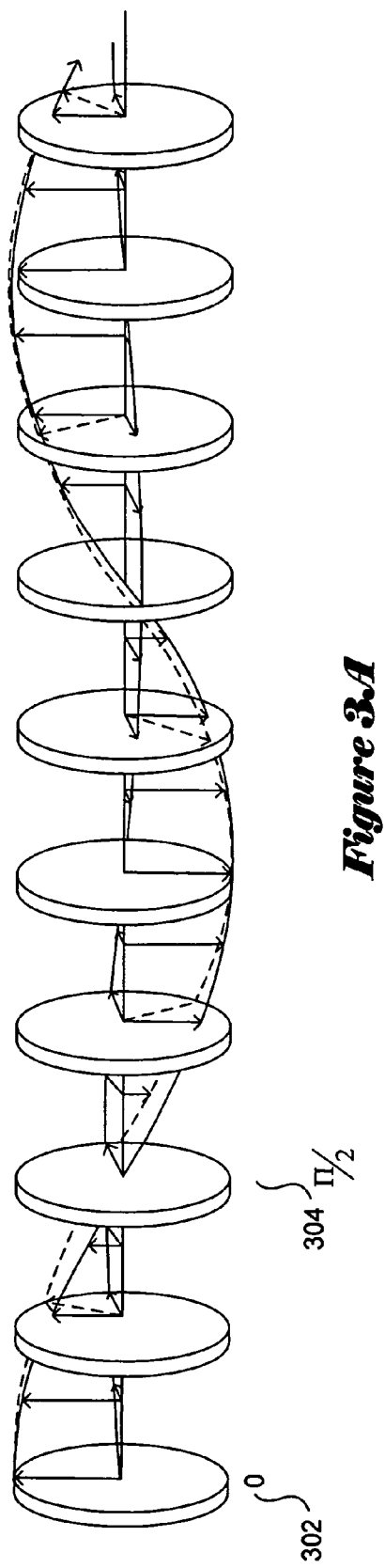
FIGS. 3A-C illustrate a circularly polarized light wave.
Figure 3B:
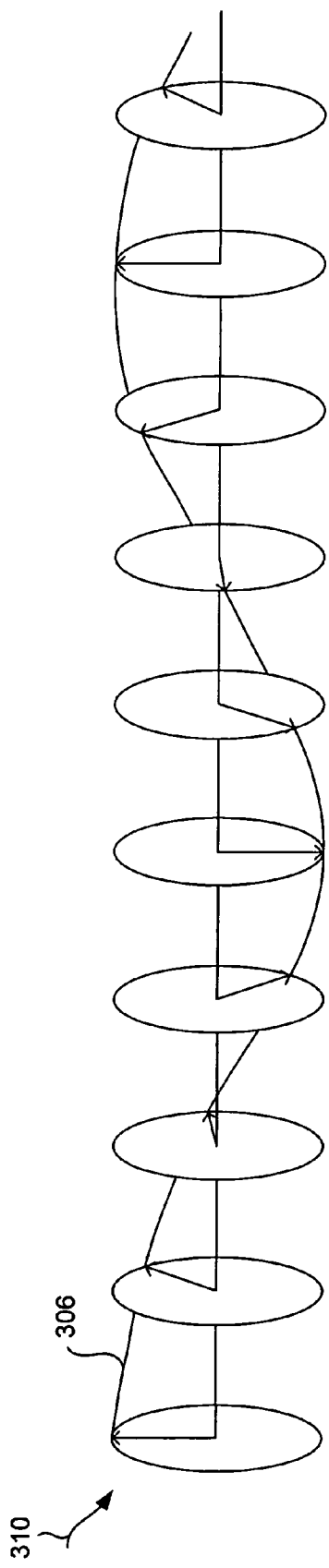
Figure 3C:
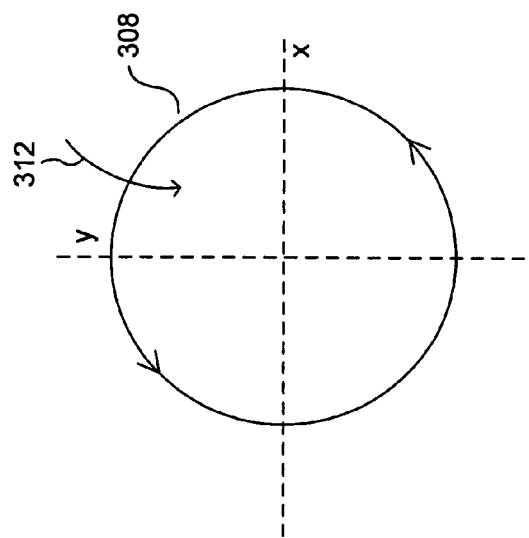

FIGS. 3A-C illustrate a circularly polarized light wave. The circularly polarized light wave is obtained, as shown in FIG. 3A, by a phase shift of the x-axis component of the plain-polarized light waves shown in FIGS. 1A and 2A with respect to the y-axis component. In other words, as shown in FIG. 3A, while the peak of the oscillation of the y-component of the light wave occurs at position 0 radians 302, the peak of the x-axis component oscillation occurs at position $$\frac{\pi}{2}$$

radians 304. When the x-axis component is phase shifted by $$\frac{\pi}{2}$$

radians in advance of the y-axis component as shown in FIG. 3A, the component electric vectors in the x and y directions at each point along the z axis add, by vector addition, to a resulting electric vector of constant magnitude. The direction of the resultant vector continuously moves in a counter-clockwise direction when viewed down the z axis. FIG. 3B shows the resultant, circularly polarized light wave 306 alone, without plots of the x-axis component and y-axis component light waves. As clearly seen in FIG. 3B, the circularly polarized light wave describes a helix parallel to, and centered about, the z axis. The z-axis projection of the electric vector is a circle 308, as shown in FIG. 3C. When viewed down the z axis in the directions indicated by arrows 310 and 312, the electric vector rotates in a counter-clockwise direction about the origin. Thus, circularly polarized light is represented by a circle in the z axis projection, in contrast to the line representation of plain-polarized light shown in FIGS. 2C and 2A. The direction of rotation of the electric vector in the z-axis projection depends on which of the two component waves is phase-advanced.

Figure 4A:
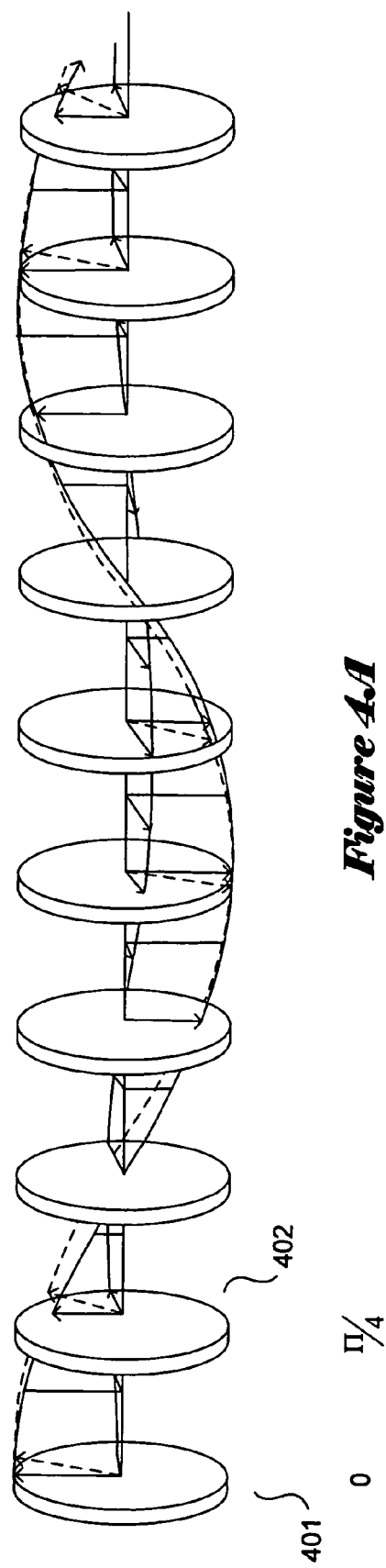
FIGS. 4A-C illustrate elliptical polarization.
Figure 4B:
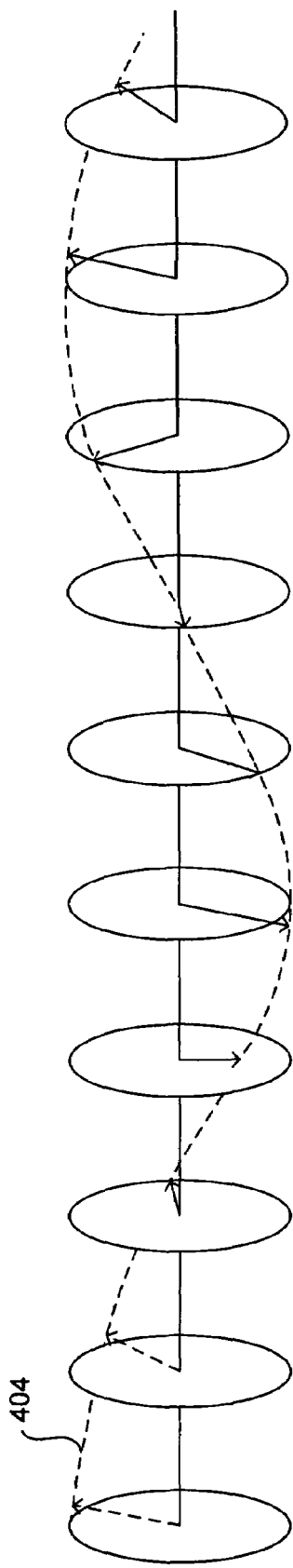
Figure 4C:
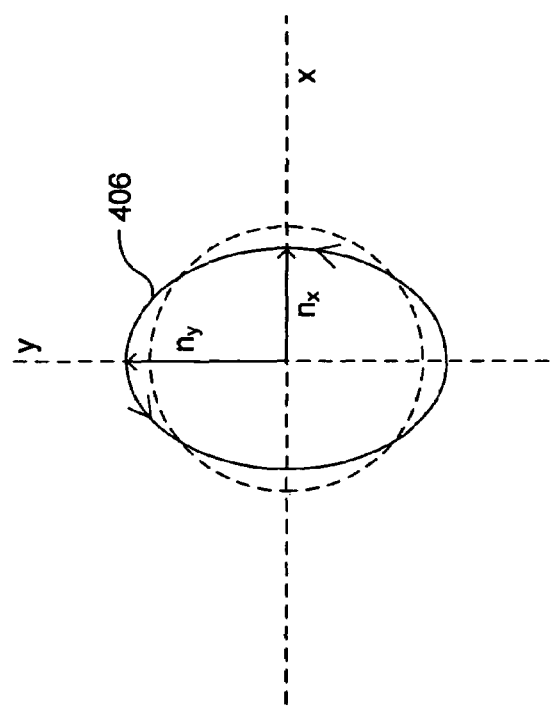

When the x-axis component and y-axis components of a plain-polarized light wave are phase shifted by an amount greater than 0 radians but less than $$\frac{\pi}{2}$$

radians, or greater than $$\frac{\pi}{2}$$

radians, but less than π radians, the resulting light wave is elliptically polarized. FIGS. 4A-C illustrate elliptical polarization. In FIG. 4A, the peak oscillation of the y-axis component of the light wave occurs at position 0 radians 401 while the peak oscillation of the x-axis component of the light wave peaks at position $$\frac{\pi}{4}$$

radians 402. The x-axis component of the light wave is thus shifted $$\frac{\pi}{4}$$

radians in advance of the y-axis component of the light wave. In this case, the electric vectors resulting from vector combination of the x-axis and y-axis electrical vectors change in both magnitude and direction along the z axis. FIG. 4B shows the resultant elliptically polarized light wave 404 without the x-axis and y-axis component light waves, clearly illustrating the helical, but eccentric, form of the light wave. FIG. 4C shows the z-axis projection of the elliptically polarized light wave. As can be seen in FIG. 4C, the elliptically polarized light wave describes, in projection, an ellipse 406, with the electric vector of the elliptically polarized light wave rotating in a counter-clockwise direction. The ellipse has a major axis in the y direction and a minor axis in the x direction.

Elliptically polarized light may occur when linearly polarized light is passed through an optically anisotropic sample. The optically anisotropic sample may show different indices of refraction in different directions, or, in other words, may show anisotropy in index of refraction. This anisotropy in index of refraction corresponds to anisotropy in the phase velocity of the light within the sample. As the index of refraction increases, the phase velocity decreases. Thus, in the examples shown in FIGS. 4A-C, the anisotropy in index of refraction is resolved into a y-axis index of refraction $n_y$ and an x-axis index of refraction and $n_x$. The ratio of the major and minor axes of the ellipse is proportional to the ratio of the indexes of refraction in the y and x directions. The major axis is referred to as the slow axis since the larger index of refraction corresponds to a slower phase velocity within the substance that generates elliptical polarization from impinging, linearly polarized light. LB is not restricted to act only on linearly polarized light. Any form of polarization that can be split into linear polarized components will experience some kind of change due to LB. In other words, circular polarized light will become elliptically polarized in general.

Figure 5:
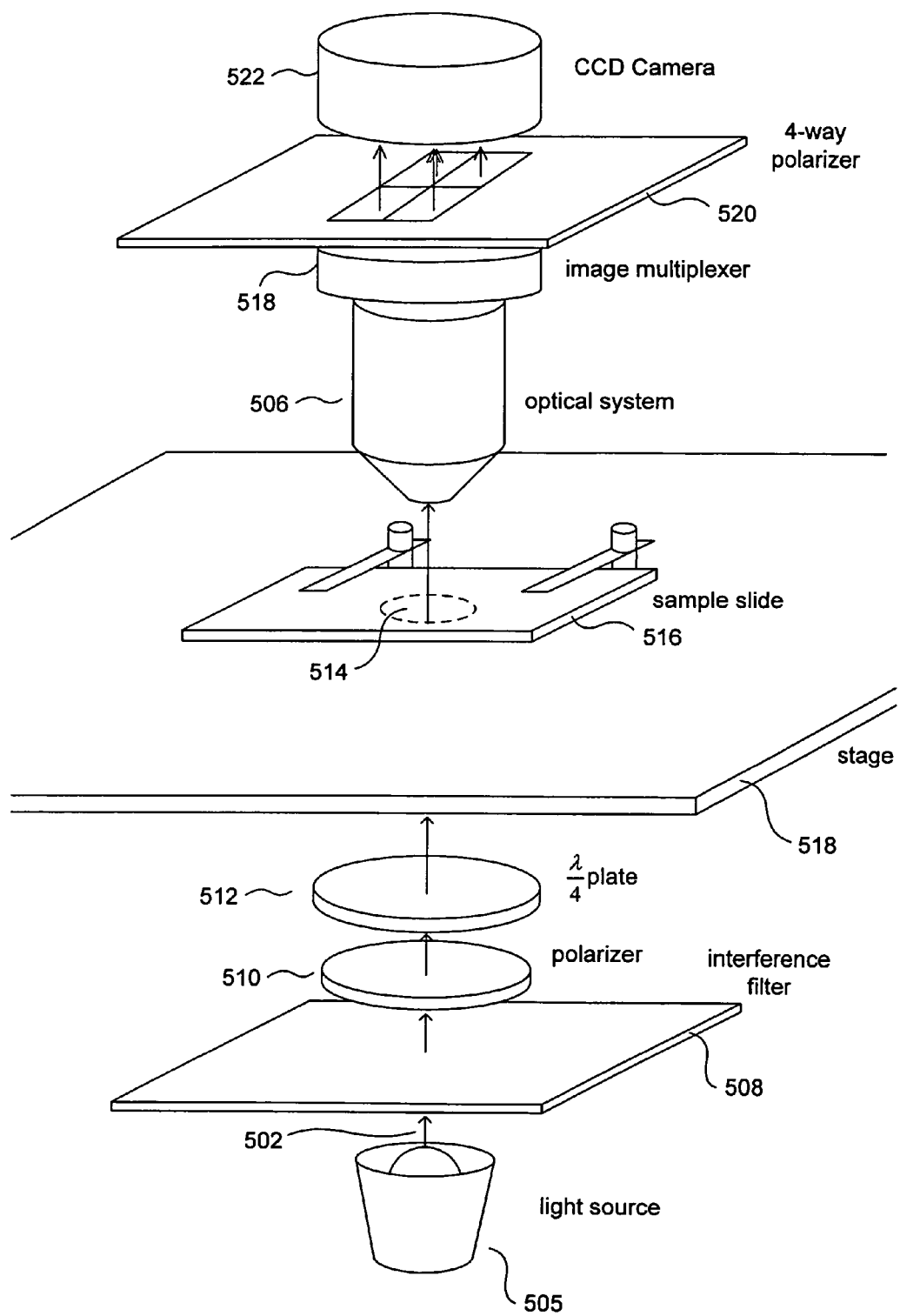
FIG. 5 illustrates one embodiment of the linear-birefringence-detecting, polarizing light microscope ("LB microscope") that represents one embodiment of the present invention.

A Linear-Birefringence-Detecting Polarizing Light Microscope that Represents One Embodiment of the Present Invention FIG. 5 illustrates one embodiment of the linear-birefringence-detecting polarizing light microscope ("LB microscope") that represents one embodiment of the present invention. In FIG. 5, vertical, upward-directed arrows, such as vertical, upward-directed arrow 502, represents the light path within the LB microscope. The microscope includes a light source 504 that directs light upwards, towards the optical system of the microscope 506. The light first passes through an interference filter 508 to select light of a desired range of wavelengths or frequencies to pass through the sample and optical system, and then through a plain-polarizer 510 to generate plain-polarized light that is directed towards the optical system. Next, the plain-polarized light is passed through a quarter-wave plate 512 that introduces a $$\frac{\pi}{4}$$

phase shift between the x-axis and y-axis components of the plain-polarized light, as discussed above with reference to FIGS. 3A-C. The quarter-wave plate 512 is orientated so that the plane of the impinging plain-polarized light falls at an angle of 45 degrees, or $$\frac{\pi}{4}$$

radians, with respect to the eigenrays of the quarter-wave plate. The circularly polarized light resulting from passing plain-polarized light through the quarter-wave plate then passes through a sample 514 on a slide 516 affixed to a stage 518. The light, potentially elliptically polarized due to passing through an optically anisotropic sample, then enters the optical system 506 of the microscope, which generates an optical image. The optical image is split into four sub-images by an optical-image multiplexer 518. Each of the four, resulting sub-images is passed through a different one of four polarizing regions of a four-way polarizer/analyzer 520 to produce four different, resultant analyzed sub-images, each one-quarter of the size of the original image produced by the optical system 506. The four analyzed sub-images impinge on a charged-coupled device camera ("CCD camera") 522 that measures the intensities of impinging light at discrete points, called pixels, within the four sub-images in real time. The intensity data is transferred at a fixed frame rate, such as a rate of 30 images per second, to a computer system which processes the images in order to produce false-color images that represent a computed linear birefringence, a computed extinction angle, and a computed transmission for each pixel in a quarter-sized representation of the original optical image produced by the optical system 506 of the LB microscope.

Figure 6:
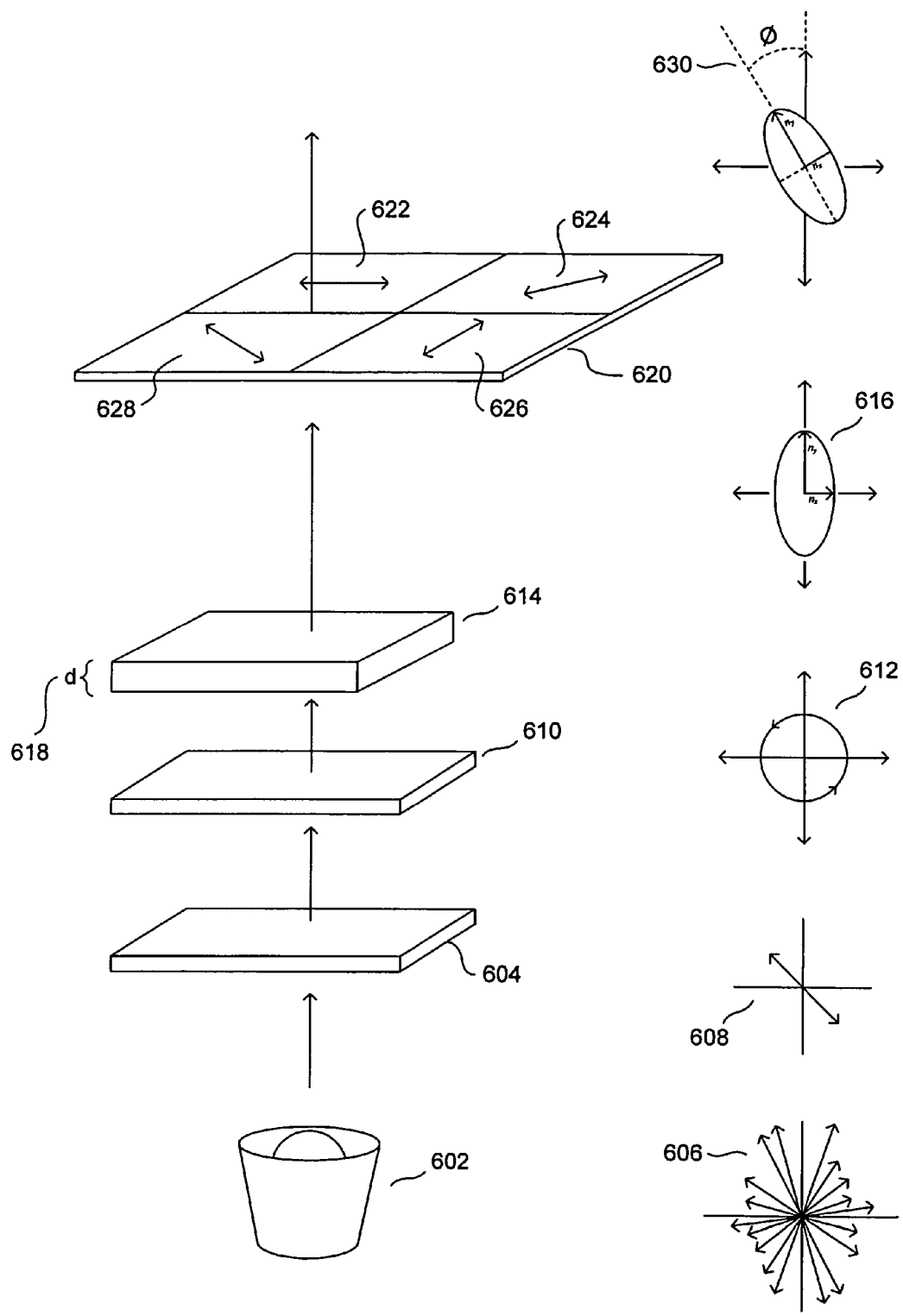
FIG. 6 shows the main optical transformation stages of the LB microscope illustrated in FIG. 5, along with z-axis-projection representations of the light waves produced by each transformation.

FIG. 6 shows the main optical transformation stages of the LB microscope illustrated in FIG. 5, along with z-axis-projection representations of the light waves produced by each transformation. Between the light source 602 and the plain polarizer 604, the monochromatic light consists of many different light waves with different orientations, shown in the z-axis projection 606. After passing through the plain polarizer 604, the light is plain polarized, as shown in the z-axis projection 608. After passing through the quarter-wave plate, or retarder, 610, the light wave is circularly polarized, as shown in the z-axis projection 612. After passing through the sample 614, the light wave may become elliptically polarized, as shown in z-axis projection 616, when the sample exhibits anisotropic index of refraction or, in other words, when the sample is optically anisotropic. The phase change δ introduced by the sample can be computed as:

$$\delta = \frac{2\pi d(n_y - n_x)}{\lambda}$$

where d is the width of the optically anisotropic sample 618, $n_y$ and $n_x$ are the y-component and x-component indices of refraction, and λ is a wavelength of the light. The light then passes through the four-way polarizer 620. The four-way polarizer has regions that polarize light at angles of zero radians 622, $$\frac{\pi}{4}$$

radians 624, $$\frac{\pi}{2}$$

radians 626, and $$\frac{3\pi}{4}$$

radians 628, with respect to a reference frame for the four-way polarizer. In general, passing of the elliptically polarized light through an analyzer, such as the four-way polarizer 620, may introduce an orientation angle φ 630 with respect to the frame of reference of the analyzer, since the sample in the LB microscope that represents one embodiment of the present invention is not oriented with respect to the analyzer. The inclination angle of the eigen modes is this orientation angle φ, also called the extinction angle.

Figure 7:
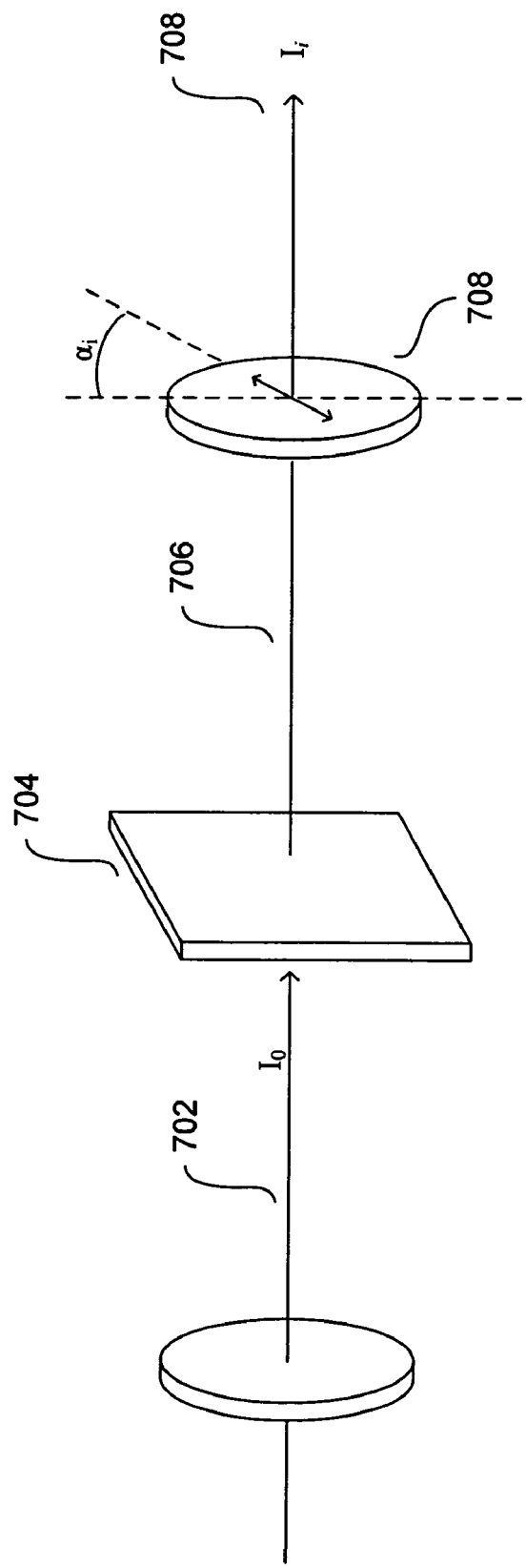
FIG. 7 shows a simplified linear-birefringence detection system as an initial illustration point for derivation of a computational analysis of captured images by the LB microscope that represents one embodiment of the present invention.

FIG. 7 shows a simplified linear-birefringence detection system as an initial illustration point for derivation of a computational analysis of captured images by the LB microscope that represents one embodiment of the present invention. In FIG. 7, plain-polarized light of intensity $I_0$ 702 passes through an optically active sample 704 to produce elliptically polarized light 706. The elliptically polarized light 706 is analyzed by a plain-polarizer analyzer 708 that is rotated through 180 degrees, or π radians, to discrete angular intervals $\alpha_i$. At each angle $\alpha_i$, the intensity $I_i$ of the light passing through the polarizer 708 is measured. The measured intensities $I_i$ are related to the initial, circularly polarized light intensity $I_0$ by the following relationship:

$$I_i = \frac{I_0}{2}[1 + \sin 2(\alpha_i - \phi)\sin\delta]$$

Using the well-known trigonometric formula:

$$\sin(x-y) = \sin(y)\cos(y) - \cos(x)\sin(y),$$

the above expression for measured intensity can be placed into polynomial form:

$$I_i = a_0 + a_1 \sin 2\alpha_i + a_2 \cos 2\alpha_i$$

where $$a_0 = \frac{I_0}{2},\ a_1 = \frac{I_0}{2}\cos 2\theta \sin\delta,\ \text{and}\ a_2 = -\frac{I_0}{2}\sin 2\theta \sin\delta.$$

In the LB microscope that represents one embodiment of the present invention, rather than measuring light intensities at a large number of angles $\alpha_i$, as in the traditional instrument illustrated in FIG. 7, the intensities are measured only at four angles 0, $$\frac{\pi}{4}, \frac{\pi}{2}, \text{ and } \frac{3\pi}{4}$$

with respect to the reference frame of the four-way polarizer. The four analyzed sub-images that result from passing the four-way multiplexed optical image through the four-way polarizer are thus characterized below in Table 1:

TABLE 1

| sub-image | polarization angle in degrees | polarization angle in radians |
|---|---|---|
| $I_1$ | 0 | 0 |
| $I_2$ | 45 | $\pi/4$ |
| $I_3$ | 90 | $\pi/2$ |
| $I_4$ | 135 | $3\pi/4$ |

The four measured intensities corresponding to the four analyzed sub-images therefore produce four different equations of the form:

$$I_i = a_0 + a_1 \sin 2\alpha_i + a_2 \cos 2\alpha_i$$

since the angles $\alpha_i$ are predetermined by the orientation of the four polarizing elements within the four-way polarizer. A traditional least-squares method can be used to compute the best values of the coefficients $a_0$, $a_1$, and $a_2$ from the measured intensities. The least-squares method provides a solution to a minimization problem in which a function D, shown below, is minimized:

$$D = \sum_{i=1}^{4} \frac{1}{w}(I_i - I_c)^2$$

where $I_i$ is an intensity measured at one of the four angles 0

$$\frac{\pi}{4}, \frac{\pi}{2}, \frac{3\pi}{4};$$

$I_c$ is the intensity computed by the above polynomial expression; and w is a weighting factor that is ignored in the following derivation.

The function D is minimal when the partial differentials of D with respect to each of the three coefficients $a_0$, $a_1$, and $a_2$ are zero:

$$\frac{\partial D}{\partial a_0} = 0$$

$$\frac{\partial D}{\partial a_1} = 0$$

$$\frac{\partial D}{\partial a_2} = 0$$

Using the notation:

$$x_{1_i} = \sin 2\alpha_i$$

$$x_{2_i} = \cos 2\alpha_i$$

the three partial differential equations become:

$$\frac{\partial D}{\partial a_0} = \sum_{i=1}^{4} 2(I_i - I_c) = 0$$

$$\frac{\partial D}{\partial a_1} = \sum_{i=1}^{4} 2(I_i - I_c)x_{1_i} = 0$$

$$\frac{\partial D}{\partial a_2} = \sum_{i=1}^{4} 2(I_i - I_c)x_{2_i} = 0$$

Using the polynomial expression for measured intensity:

$$I_i = a_0 + a_1 \sin 2\alpha_i + a_2 \cos 2\alpha_i,$$

the above three partial differential equations can be represented, in matrix form, as:

$$\begin{pmatrix} \sum_{i=1}^{4} I_i \\ \sum_{i=1}^{4} I_i x_{1_i} \\ \sum_{i=1}^{4} I_i x_{2_i} \end{pmatrix} = \begin{pmatrix} \sum_{i=1}^{4} 1 & \sum_{i=1}^{4} x_{1_i} & \sum_{i=1}^{4} x_{2_i} \\ \sum_{i=1}^{4} x_{1_i} & \sum_{i=1}^{4} x_{1_i}^2 & \sum_{i=1}^{4} x_{2_i} x_{1_i} \\ \sum_{i=1}^{4} x_{2_i} & \sum_{i=1}^{4} x_{1_i} x_{2_i} & \sum_{i=1}^{4} x_{2_i}^2 \end{pmatrix} \begin{pmatrix} a_0 \\ a_1 \\ a_2 \end{pmatrix}$$

The following table summarizes the values of $x_1$ and $x_2$ at the four measured angles $\alpha_i$ for the LB microscope that represents one embodiment of the present invention:

TABLE 2

| angle $\alpha_i$ | $x_{1_i} = \sin 2\alpha_i$ | $x_{2_i} = \cos 2\alpha_i$ |
|---|---|---|
| 0 | 0 | 1 |
| $\frac{\pi}{4}$ | 1 | 0 |
| $\frac{\pi}{2}$ | 0 | -1 |
| $\frac{3\pi}{4}$ | -1 | 0 |

Using these values to compute the sums in the above matrix equation, the matrix equation can be simplified to:

$$\begin{pmatrix} I_1 + I_2 + I_3 + I_4 \\ I_2 - I_4 \\ I_1 - I_3 \end{pmatrix} = \begin{pmatrix} 4 & 0 & 0 \\ 0 & 2 & 0 \\ 0 & 0 & 2 \end{pmatrix} \begin{pmatrix} a_0 \\ a_1 \\ a_2 \end{pmatrix}$$

Because the 3×3 matrix is diagonal, the inverse of this matrix is easily computed as a diagonal matrix with elements having values reciprocal to the 3×3 matrix. Therefor, multiplying both sides of the above matrix equation from the left by the inverse 3×3 matrix, one obtains:

$$\begin{pmatrix} \frac{1}{4} & 0 & 0 \\ 0 & \frac{1}{2} & 0 \\ 0 & 0 & \frac{1}{2} \end{pmatrix} \begin{pmatrix} I_1 + I_2 + I_3 + I_4 \\ I_2 - I_4 \\ I_1 - I_3 \end{pmatrix} = \begin{pmatrix} a_0 \\ a_1 \\ a_2 \end{pmatrix}$$

Multiplying the measured-intensity vector by the inverse matrix, in the above equation, results in the following three expressions for the coefficients $a_0$, $a_1$, and $a_2$:

$$a_0 = \frac{I_1 + I_2 + I_3 + I_4}{4}$$
$$a_1 = \frac{I_2 - I_4}{2}$$
$$a_2 = \frac{I_1 - I_3}{2}$$

The birefringence, extinction angle θ, and transmission for the optical image captured from the LB microscope can be computed on a pixel-by-pixel basis, using the above-obtained results. The birefringence is computed as:

$$birefringence = |\sin\delta| = \frac{1}{a_0}\sqrt{a_1^2 + a_2^2}$$

where the computed birefringence ranges in value from 0, indicating no birefringence, to 1, indicating maximal birefringence.

Extinction angles are computed as:

$$\text{extinction angle} \phi = \frac{\pi}{2} + \text{sign}(a_2)\frac{1}{2}\cos^{-1}\left(\frac{-a_1}{\sqrt{a_1^2 + a_2^2}}\right)$$

where the computed extinction angle ranges from 0 to π, and corresponds to the orientation angle of the slow, or major, axis of the ellipse in the z-axis projection of elliptically polarized light with respect to the frame of reference of the four-way polarizer/analyzer.

The transmission is computed as:

$$a_0$$

where the computed transmission ranges from zero, representing opacity, to one, representing full transmission of the light impinging on the sample.

Figure 8A:
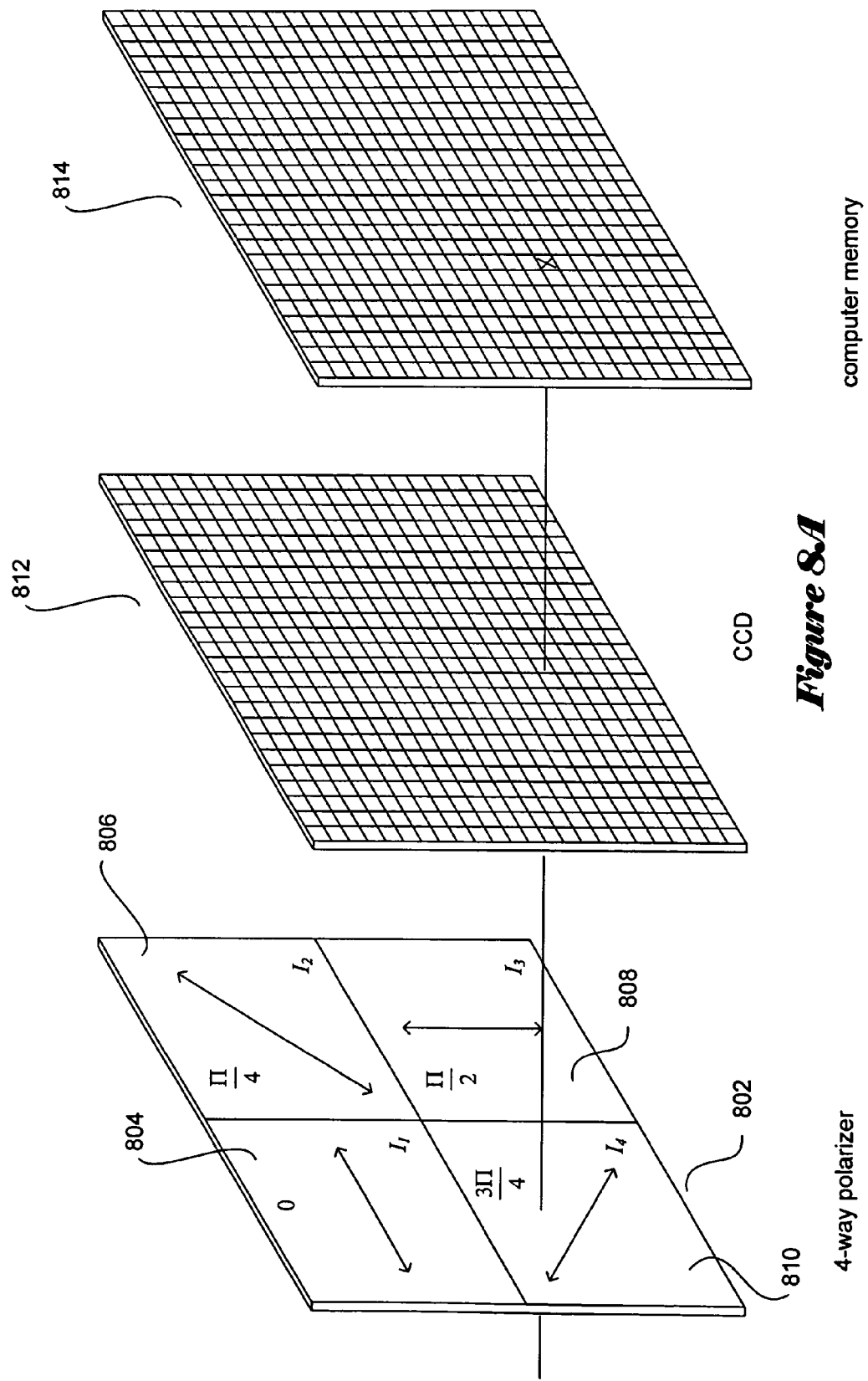

FIGS. 8A-B illustrate capture and computational processing of the four-way multiplexed and four-way analyzed image by a processing component the LB-microscope system that represents one embodiment of the present invention. As shown in FIG. 8A, and as discussed above, the four-way multiplexed image is passed through the four-way polarizer 802 with sub-polarizers oriented at angles of 0 radians 804, $$\frac{\pi}{4}$$

radians 806, $$\frac{\pi}{2}$$

radians 808, and $$\frac{3\pi}{4}$$

radians 810. The four analyzed sub-images are then captured by the CCD camera 812 and transferred, as fixed-size pixel intensities within an array of pixel intensities corresponding to the array of detectors within the CCD camera, by the CCD camera to a buffer in an electronic memory 814. Beginning with the raw data transferred from the CCD camera to the electronic memory (816 in FIG. 8B), the raw data comprising the four sub-arrays $I_1$, $I_2$, $I_3$, and $I_4$ is first normalized with respect to a stored image produced without the plane polarizer, quarter-wave plate, and sample to produce four, normalized sub-arrays 817 $I'_1$, $I'_2$, $I'_3$, and $I'_4$, and false-color images representing the computed birefringence 818, computed extinction angle 819, and computed transmission 820 for each pixel of a quarter-sized representation of the initial optical image generated by the optical components of the LB microscope are generated from the four normalized sub-arrays $I'_1$, $I'_2$, $I'_3$, and $I'_4$ using the above-derived computations based on optimizing values of the coefficients $a_0$, $a_1$, and $a_2$ on a pixel-by-pixel basis.

Figure 9A:
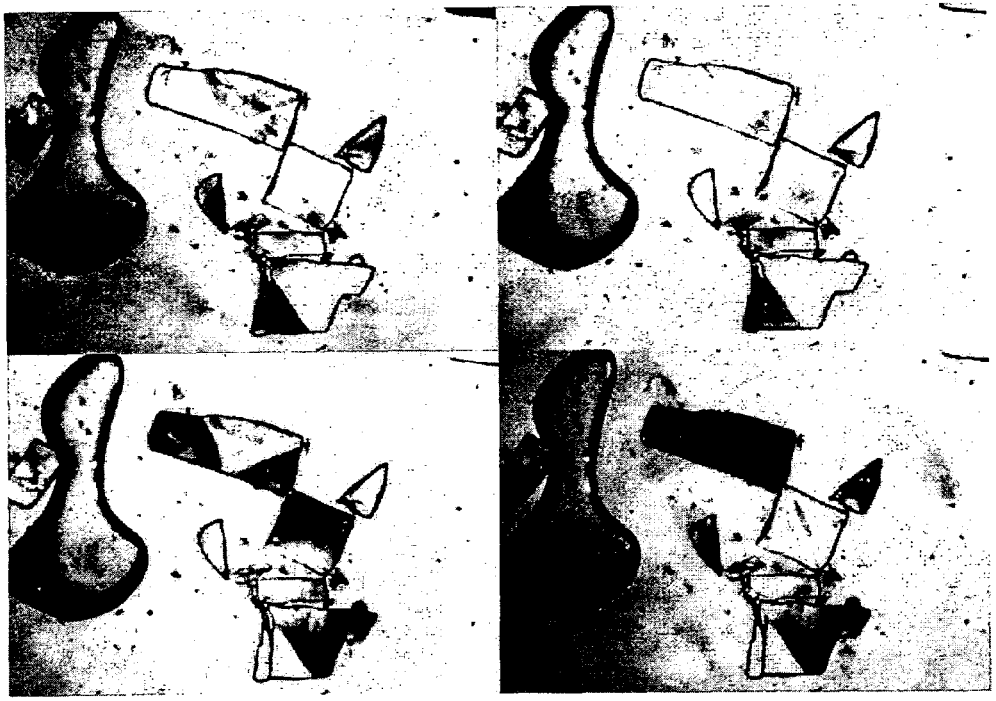
FIGS. 9A-B show examples of a four-way-polarizer-analyzed optical image recorded by the CCD camera of an LB microscope that represents one embodiment of the present invention and the computer-generated output that displays representations of polarization phenomena detected in the four-way analyzed image.
Figure 9B:
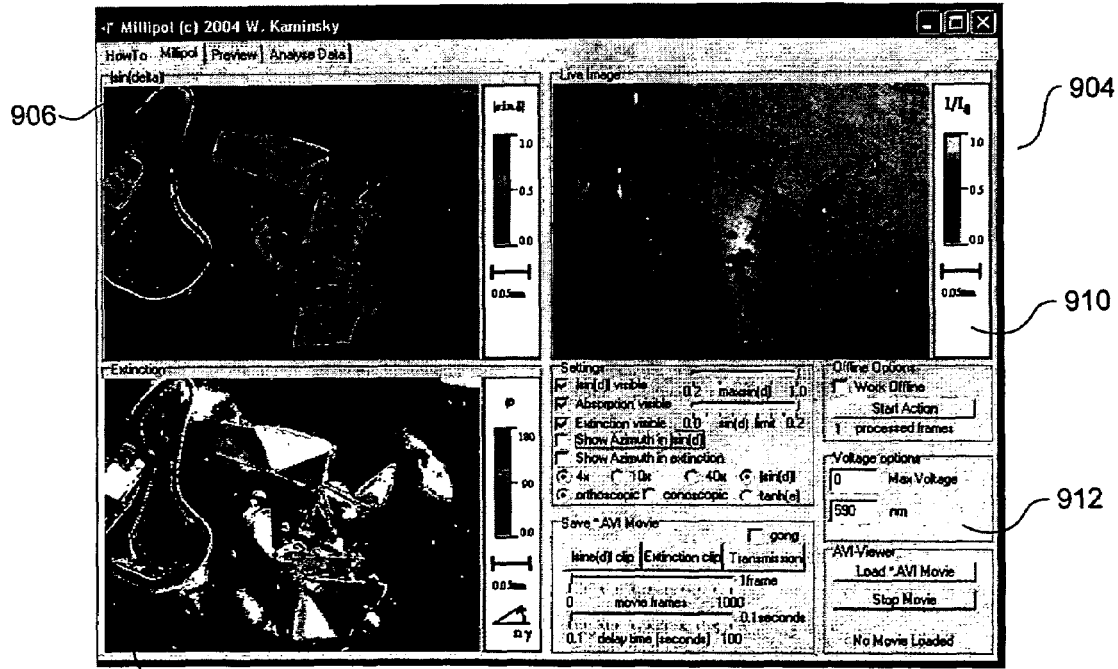

FIGS. 9A-B show examples of a four-way-polarizer-analyzed optical image recorded by the CCD camera of an LB microscope that represents one embodiment of the present invention and the computer-generated output that displays representations of polarization phenomena detected in the four-way analyzed image. The four-way analyzed image shown in FIG. 9A is generated from a solution of tiny crystals in a sample well of a slide within the LB microscope. Notice that a diagonal portion of the lowest crystal in each of the four images is darkly colored in the 0 radian and $$\frac{\pi}{4}$$

radian images, but is lightly colored in the $$\frac{\pi}{2}$$

radian and $$\frac{3\pi}{4}$$

radian images. Other portions of the crystals show cyclical patterns of lightness and darkness over the four images. Note, however, that the large, dumbbell-shaped object in the images is not markedly changed in shading over the four images. The computer-generated output from the LB microscope is shown in a four-paned window 904. A first window 906 displays the computed birefringence at each pixel in a quarter-sized version of the originally captured optical image. Note that the computed birefringence is lighter, and thus greater in value, for the regions of the image corresponding to the angular-shaped crystals than for the surrounding solution and the dumbbell-shaped object. A second pane 908 shows the computed extinction angle for each pixel within a quarter-sized representation of the originally captured optical image. Note that the birefringent crystals generally have larger extinction angles than the dumbbell-shaped object and surrounding solution. A third pane 910 shows the transmission computed for each pixel of a quarter-sized representation of the originally captured optical image. Finally, a fourth pane 912 provides an interface through which a user may customize the displayed output by choosing which of the false-color images to display, by choosing a magnification to select related calibration files, and by choosing to either view computer-generated false-color images in real time or to view computer-generated false-color images from stored data.

There are many different possible encodings of computed birefringence, extinction angle, and transmission. In one embodiment of the present invention, the computed, numeric values for birefringence, extinction angle, and transmission are encoded linearly in one color channel, for example the red color channel, and the two other color channels are computed to vary sinusoidally over the ranges of linearly encoded birefringence, extinction angle, and transmission values. This encoding allows the computed birefringence, extinction angle, and transmission values to be recovered directly from stored images and video files. Many other types of encodings are possible.

In a crystal-detecting application, the LB microscope can generate the false-color images from which regions of the image exhibiting birefringence can be easily identified. In the example false-color images shown in FIG. 9B, the dumbbell-shaped object is clearly not crystalline. In fact, the dumbbell-shaped object was determined to be a bubble. Unfortunately, crystals are not easily detected by shape. Protein crystals can appear to have rounded, or curved surfaces, and amorphous impurities can often have angular shapes. The LB microscope can be used as the basis for an automated crystal detecting system. The LB microscope is particularly suited for this application, since the samples need not be oriented with respect to an internal frame of reference, thus avoiding expensive mechanical manipulation of crystallization solutions that can lead to inhibition of further crystal growth. Furthermore, real-time image capture and processing can save huge amounts of time when thousands or hundreds of thousands of crystallization solutions need to be imaged. Additional image processing can be used to determine the regions of images which exhibit birefringence, and to further process the data collected from those regions in order to determine the volume of detected crystals, and to make empirical determinations of crystal quality.

Computational Processing of Captured Images

In order to capture four-way multiplexed and analyzed images from the LB microscope that represents one embodiment of the present invention, and in order to computationally analyze the captured images and produce the false-color images that represent the computed birefringence, extinction angles, and transmission on a pixel-by-pixel basis, the CCD-camera-captured image data need to be efficiently stored in computer memory and efficiently manipulated, so that false-color images can be generated and displayed at a reasonable frequency, such as a frequency of capture provided by third-party image-capture software. In one embodiment of the present invention, images are captured and processed at a rate of 30 images per second.

Figure 10:
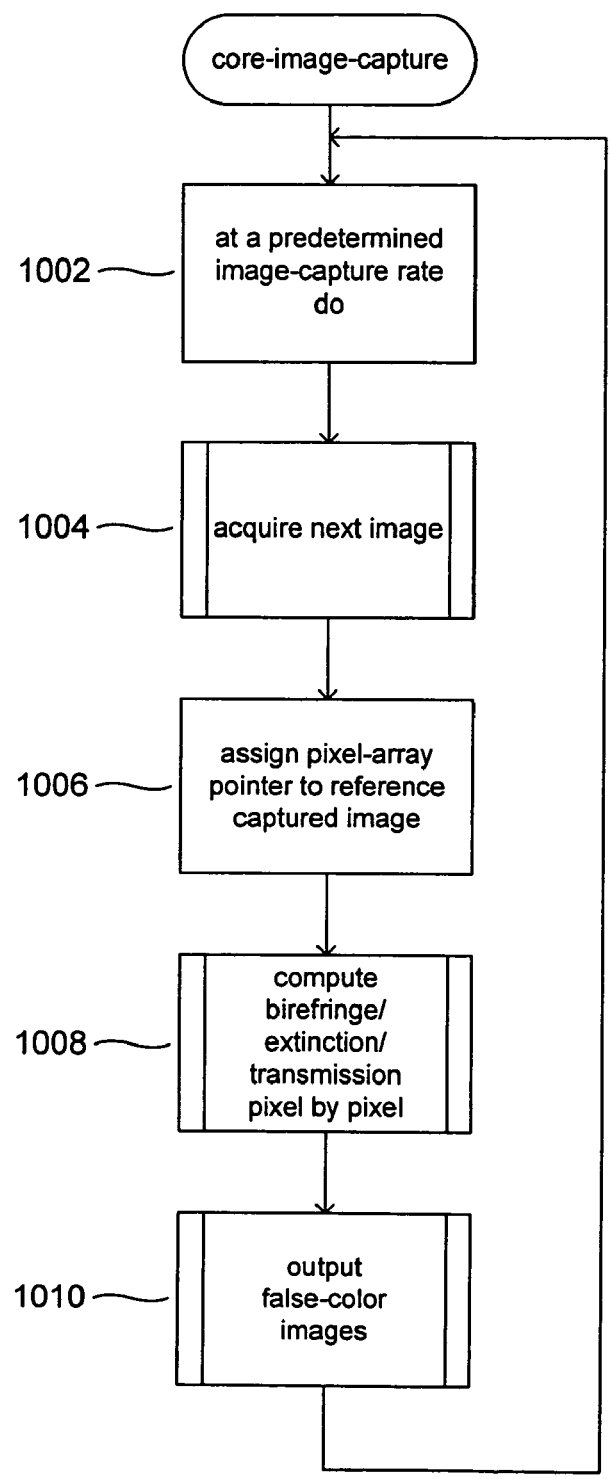
FIG. 10 is a control-flow diagram for the core image-capture and image-processing loop of a computer program that represents one embodiment of the present invention.

FIG. 10 is a control-flow diagram for the core image-capture and image-processing loop of a computer program that represents one embodiment of the present invention. This core loop is shown, in FIG. 10, to iterate endlessly, although, in practice, the loop is launched and terminated from the enclosing computer program. Step 1002 represents an endless do-loop that iterates at a predetermined image-capture rate. In step 1004, the next image generated by the CCD camera is captured in computer memory. This step may be carried out by any of numerous third-party image-capture software packages or by specially-developed routines that interface with input ports and operating-system drivers. Then, in step 1006, a pixel-array pointer is initialized to reference the captured image. This is a fundamental operation for the real-time image-capture and image-processing loop that represents one embodiment of the present invention. In many commercially available image processing routines, the data generated by a CCD camera is first moved into a computer-memory buffer for storing bit maps, from which it is then copied to a pixel array for manipulation by familiar array-based operations. However, for real-time capture and processing of images, such internal memory copies are prohibitively expensive in time. For a real-time system, it is important that the memory buffer to which the CCD-camera data is written is doubly used as a pixel array for image manipulation and processing, without internal memory copies. In step 1008, the birefringence, extinction angle, and transmission are computed on a pixel-by-pixel basis, as discussed above, for each pixel in a quarter-sized representation of the originally captured optical image. Finally, in step 1010, quarter-sized false-color images that represent the computed birefringence, extinction angle, and transmission generated an output to a user interface, such as the user interface shown in FIG. 9D, displayed on a computer screen. Any of a variety of intensity-and-color-coding schemes can be used to represent the range of values described above for the per-pixel computed birefringence, extinction angle, and transmission.

Figure 11:
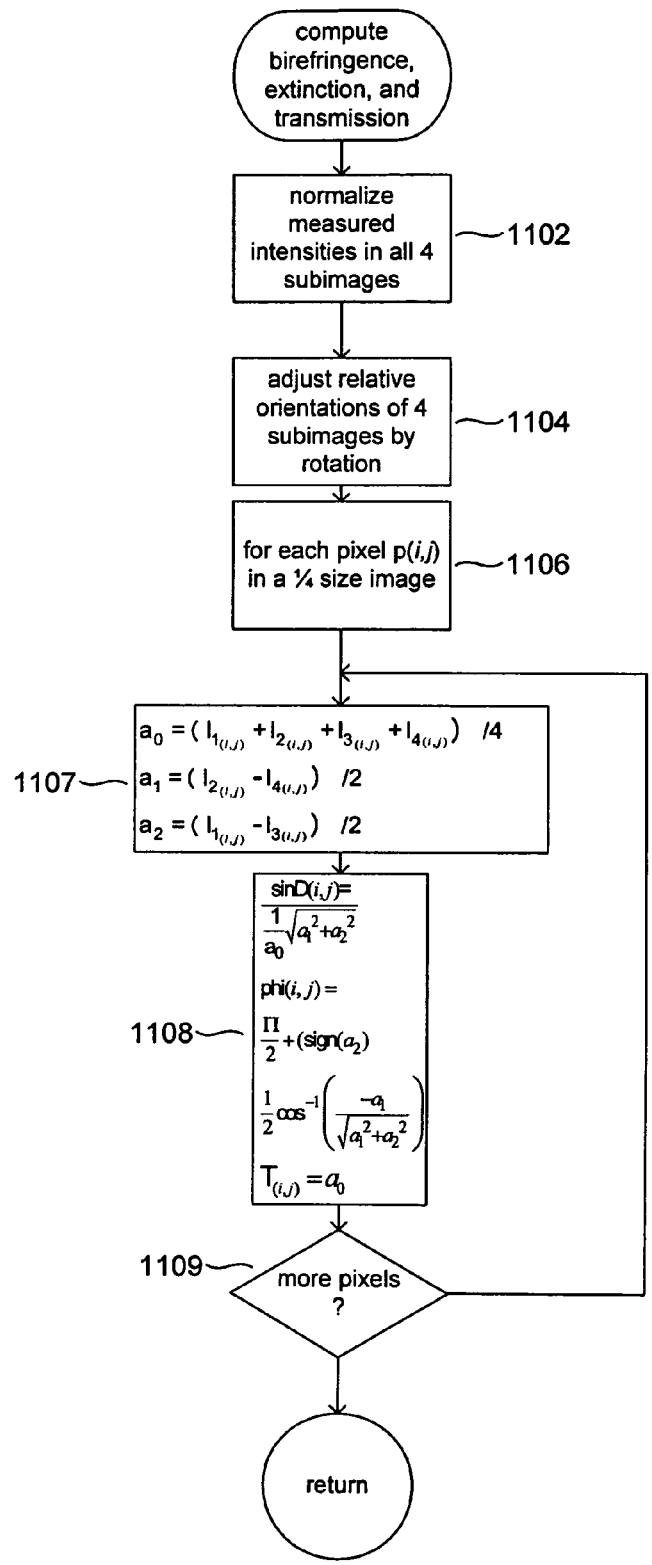
FIG. 11 shows a control-flow diagram for the computation of birefringence, extinction angle, and transmission in step 1008 of FIG. 10.

FIG. 11 shows a control-flow diagram for the computation of birefringence, extinction angle, and transmission in step 1008 of FIG. 10. In a first step 1102, the raw data is normalized by multiplying the raw intensity values by corresponding pixel values obtained from the LB microscope without a sample present. This operation normalizes the four sub-images with respect to one another, and removes certain systematic intensity errors that may be present in the instrument. Next, in step 1104, the orientations of the four sub-images captured by the CCD camera may be adjusted, so that all four sub-images are aligned with one another. Then, in the for-loop of steps 1106-1109, the linear birefringence, extinction angle, and transmission are computed for each pixel in a quarter-sized representation of the originally captured optical image, generating three quarter-sized pixel arrays with intensity/color values representing the computer birefringence, extinction angle, and transmission, respectively.

Next, a portion of one embodiment of the computational software that carries out image capture and processing by an LB microscope that represents one embodiment of the present invention is discussed. The computer program is written in object-oriented Pascal. This computer program includes a core image capture and processing routine that iterates at a selected image-capture frequency for a particular LB microscope, extensive code for generating the user interface shown in FIG. 9B and additional user interfaces, and also extensive initialization code and routines used for image capture and image processing. The core image-capture and image-processing loop of the computer program that represents one embodiment of the present invention is next provided:

```
1       TColorArray = array[0..MaxInt div SizeOf(TRGBQuad)–1] of TRGBQuad;
2       PColorArray = ^TColorArray;
3       function BmpToArray(const aBitmap: TBitmap): PColorArray;
4       procedure BmpFromArray(var aBitmap: TBitmap; p: Pointer; w,h: Integer);
5       FFrameStream   :TMemoryStream;      //stream for read a frame
6       FFrameBitmap   :TBitmap;       //bitmap contain the last frame
7       PColors: PColorArray;
8   function TForm1.BmpToArray(const aBitmap: TBitmap): PColorArray;
9   Var i:integer;
        row:PColorArray;
10  begin
11      w := aBitmap.Width;
12      h := aBitmap.Height;
13      abitmap.pixelformat := pf32bit;
14      For i:=0 to abitmap.Height–1 do begin
15          row:=abitmap.Scanline[i];
16      end;
17      Result := row;
18  end;
19      procedure TForm1.BmpFromArray(var aBitmap: TBitmap; p: Pointer; w,h: Integer);
20  begin
21      with bmi.bmiHeader do begin
22          biWidth := w;
23          biHeight := –h;
24      end;
25  SetDIBits(aBitmap.Canvas.Handle,aBitmap.Handle,0,h,p,bmi,DIB_RGB_COLORS);
26  end;
27      procedure TForm1.MilliscanClick(Sender: TObject);
28      Var  i,j,k,I1,I2,I3,I4,S0,S1,S2,rr,rs:Integer;
29              f,g,q:extended;
30              BR,BB,BG,BA,AA:BYTE;
31              finished:boolean;
32      begin
33      Stopscan:=false; // if true, this routine will not be activated again
34      // Would not make much sense to run this if there is no camera attached
35      if (not havevideo) then if (not offline.Checked) then exit;
36      // If the user wants to run offline, we should not
    //try to load an image from the camera
37      If not offline.checked then begin
38          // now get an image, assign it to invisible storage image
39          // the grabbed image cannot be changed fastly, the created one can
40          if not importimage.Checked then begin
41              BtnGrabFrameNoStopClick(Sender);
42              FFrameStream.Position := 0;
43              FFrameBitmap.LoadFromStream(FFrameStream);
44              image1.picture.bitmap.Assign(FFrameBitmap);
45              end else image1.picture.bitmap.LoadFromFile('testimage.bmp');
46              // may load an image from file for testing
47      end;
48      //if desired sound signal to indicate when an image has been found
49      If gong.checked then beep;
50      try   // if things fail for any reason, try again, see end of this procedure
51          finished:=false;         // we just started
52          Bitmap := TBitmap.Create;       //make a new bitmap on the fly that
53                      // can be manipulated
54          Bitmap.FreeImage;       //get rid of old data and get memory
55          w := Image1.Picture.bitmap.Width;     // assign width
56          h := Image1.Picture.bitmap.Height;    // and height
57          bitmap.Assign(image1.Picture.Bitmap); //move pointer of grabbed image
58                      // to created one
59          PColors := BmpToArray(bitmap);         // move pointer of created image
60                      // to array
61          if not calibrated then exit;           // if we have not loaded the calibration
62                      //we should exit here and try later
63      // Normalize the image intensity to a previously saved raw image without
64      // sample and polarizers
65      If haveintensitycalibration and not importimage.checked then begin
66          For j:=0 to 639 do
67              For i:=0 to 479 do
68                  PColors[j + i*w].rgbRed :=
69                      round(PColors[j + i*w].rgbRed*Intensitycorrectionarray[j,i]);
70          end;
71      // We scan through the pixels of one qudrant in i and j ------> main loops
72      For i:=0 to 239 do
73          For j:=0 to 319 do begin;
74              // the quadrants of the camera image need to be slightly rotated
75              // towards each other, and that quickly
```

-continued

```
76        If not importimage.Checked then begin;
77             rr:=round(j/40)+i;
78             if rr<0 then rr:=0;
79             if rr>239 then rr:=239;
80             rs:=j-round(i/30);
81             if rs<0 then rs:=0;
82             if rs>319 then rs:=319;
83        end else begin;
84        // a test imgage is of course perfect and needs no rotation adjustment
85             rr:=i;rs:=j
86        end;
87        I2:= PColors[j + (i)*w].rgbRed;
88        I1:= PColors[j+320 + (i)*w].rgbRed;
89        I4:= PColors[rs + (rr+240)*w].rgbRed;
90        I3:= PColors[rs+320 + (rr+240)*w].rgbRed;
91        // Correction of polarized intensities
92        If not importimage.Checked then begin;
93             I1:=round(I1*1.00); // scale total intensities
94             I2:=round(I2*1.05); // to compensate for non-perfect
95             I3:=round(I3*1.2); // quarterwave plate
96        end else begin
97             I1:=round(I1*1.10);
98             I4:=round(I4*1.10);
99        end;
100       S0:=(I1+I2+I3+I4) div 4;// Intensity average
101       S1:= (I2 − I4)div 2 ; // half of intensity difference second-fourth
102                             //quadrant
103       S2:= (I1 − I3) div 2 ; // half of intensity difference first-third
104                             //quadrant
105       g:=root[S1*S1+S2*S2]; // call root-array for faster calculation of
106                             // root of argument, defined in From1.activate
107                             // This expression is used to calculate sin(d)
108       If g=0 then g:=0.0001 ; // better to avoid devision by 0
109       f:= (S1)/g;             // prepare calculation of extinction angle,
110                             // needed below
111                             // Capture numerical exceptions
112       If f>0.99 then f:=0.99; If f<−0.99 then f:=−0.99;
113        AA:=round(128-sign(S2)*ACS[round((1+f)*100)]) ;
114                             // Calculate extinction angle, using preset
115                             // arcustangens, defined in From1.activate
116       phiarray[j,i]:= AA; // store the result in array at appropriate
117                             //position
118       if s0>127 then s0:=127; // capture over-range values for plotting
119                             // intensity
120       if S0<1 then S0:=1;    // capture under-range values for plotting
121                             //intensity
122       S0array0[j,i] := S0; //store the result in array at appropriate
123                             //position
124            try             // scale the signal to represent correct
125                             // readings for sin(d)
126                             // using preset calibration values, defined
127                             // in From1.activate
128            if corr1[AA]>0 then q:=g/S0*255/corr1[AA]-corr0[AA];
129            If q>1 then q:=1;   // capture over-range values for plotting intensity
130            if q<0 then q:=0;   // capture under-range values for plotting intensity
131                      //scale and calculate sin(d) result, store in array
132            sinDarray[j,i]:= round(255*q/maxsind);
133            except             // capture exceptions and do nothing
134        end;                   // end of j-loop
135       end;                    // end of i-loop
136 // Now that we have transmission, extinction and sin(d) images,
137 // decide what to plot on screen
138 if sindVisible.checked then begin // if wanted, make a plot of sin(d)
139       For i:=0 to 239 do
140            For j:=0 to 319 do begin;
141                 if S0array[j,239-i]>20 then begin;
142                 // if intensity sufficient, plot sin(d), else plot a black pixel
143                 Br:=sinDarray[j,239-i];
144                 // to do so, grab a pixel
145                 PColors[j + (i)*w].rgbRed:=Br;
146                 // the red color is linear to the calculated sin(d)
147                 PColors[j + (i)*w].rgbGreen:=gr[BR];
148                 // the green one is scaled to give false colors
149                 PColors[j + (i)*w].rgbBlue:=Bl[BR];
150                 // the blue pixel is scaled as well for false color representation
151                 // gr[..] and bl[..] are defined in defined in From1.activate
152            end else begin
153                 sinDarray[j,239-i]:=0;
154                 PColors[j + (i)*w].rgbRed:=0;
```

```
155                 PColors[j + (i)*w].rgbGreen:=0;
156                 PColors[j + (i)*w].rgbBlue:= 0 ;
157              end;
158          end;
159          BMPFromArray(Bitmap,PColors,w ,h );
160          // move the array pointers into created bitmap
161          image2.picture.bitmap := bitmap;
162          // finally move pointer of created bitmap to that on screen
163          // if requested draw into that image the azimuth lines
164          if showAzimuthinSind.Checked then showazimuth2click(sender);
165       end;
166       if extinctionVisible.Checked then Begin
167       // if wanted, make a plot of extinction analogue to above
168          For i:=0 to 239 do
169             For j:=0 to 319 do begin;
170             BA:=phiarray[j,239-i];
171             If tanhe.Checked then begin
172             BA:=BA-60;
173             if BA<0 then BA:=BA+255;
174             end;
175             If sinDarray[j,239-i]>sindthreshhold/maxsind then begin
176                 PColors[j + (i)*w].rgbRed:= BA ;
177                 PColors[j + (i)*w].rgbGreen:=gr[BA];
178                 PColors[j + (i)*w].rgbBlue:= Bl[BA] ;
179             end else begin
180                 PColors[j + (i)*w].rgbRed:= 0;
181                 PColors[j + (i)*w].rgbGreen:=0;
182                 PColors[j + (i)*w].rgbBlue:= 0 ;
183             end;
184          end;
185             BMPFromArray(bitmap,PColors,w ,h );
186             image3.picture.bitmap := bitmap;
187          if showAzimuthinExtinction.Checked then azimuth1(Sender) ;
188       end;
189       if absorptionVisible.Checked then begin
190       // if wanted, make a plot of transmission analogue to above
191          For i:=0 to 239 do
192             For j:=0 to 319 do begin;
193                 BA:=(2*S0Array[j,239-i]) ;
194                 PColors[j + (i)*w].rgbRed:= BA ;
195                 PColors[j + (i)*w].rgbGreen:= BA;
196                 PColors[j + (i)*w].rgbBlue:= BA ;
197             end;
198             BMPFromArray(bitmap,PColors,w ,h );
199             image4.picture.bitmap := bitmap;
200          end;
201          finished:=true;
202       FINALLY
203          //remove created bitmap from memory
204             Bitmap.Free;
205          // Activate timer 2 to call the whole procedure again for online
206          //measurements
207          if not recording then timer2.Enabled:=true ;
208       end;
209             // otherwize call the recording procedure which will save a movie
210             // and calls this routine after each new image
211    end;
```

On lines 1 and 2, above, declarations for the pixel-array pointer "PColorArray" and a pixel array "TColor array" are provided. The function "BmpToArray" on lines 8-18 generates a pointer reference to an in-memory buffer containing bitmap data downloaded from the CCD camera. Thus, this function, along with the pixel-array-pointer type "PColorArray" allows for an in-memory buffer containing CCD-generated data to be used, in place, as a pixel array, without internal copying or expensive transformation. The core loop of the computer program that represents one embodiment of the present invention is included on lines 27-214. A next image is captured from the CCD camera on lines 40-45. On line 59, the variable "PColors" of type "PColorArray" is set to reference the bitmap buffer in which the CCD image is loaded. Again, this does not require in-memory copy of the buffer to a pixel array, but instead allows the buffer to be used as a pixel array. On lines 65-70, the captured image is normalized. On lines 72-86, the captured sub-images are rotated with respect to one another in order to align all four sub-images, when necessary. On lines 87-132, the birefringence, extinction angle, and transmission are computed on a pixel-by-pixel basis for a quarter-sized representation of the originally captured optical image. In the remaining portions of the core loop, the false-color images representing birefringence, extinction angle, and transmission are computed and stored for output to the user interface.

The described LB-microscope embodiment of the present invention may find a wide variety of uses in many different fields and applications. As one example, the LB microscope can be incorporated into an automated system for optically analyzing large arrays of crystallization experiments in order to detect the presence of crystals in solution. This application of the LB microscope can facilitate high-throughput structure determination for biological molecules that is an essential task in the emerging fields of proteomics, structural genomics, and structural biology. Current polarizing microscopes are unsuitable for this task since they depend on mechanically moving parts, orientation of a sample with respect to a frame of reference with the microscope, and computationally intensive and time-consuming image processing. Additional applications include analysis of many different types of biological samples in order to detect particular ordered arrangements of biological molecules, such as the protein amyloid A in amyloid plaques in brain tissue. There are many materials-science applications, including monitoring and quantifying mechanical stress in polymeric and crystalline materials, general contrast enhancement for imaging of materials, and other such uses.

In the described embodiments, orthoscopic images are generated and processed. In alternative embodiments, conoscopic images obtained from the back-focal plane of the optical system, and that represent images of the light source, can be generated and processed in order to calculate and display phase retardance and extinction angles arising from light passing through birefringent samples. Many additional alternative embodiments can employ different physical configurations of the optical system in order to measure different polarization states and effects. For example, when no quarter-wave plate is present, optical activity in the absence of birefringence can be measured and displayed. As another example, when neither a quarter-wave plate nor a plane polarizer is present, linear dichroism can be measured and displayed. In yet an additional example, when no quarter-wave plate is present, and an etch filter is inserted in the optical path, anisotropic fluorescent emission from a sample can be measured and displayed.

Although the present invention has been described in terms of particular embodiments, it is not intended that the invention be limited to these embodiments. Modifications within the spirit of the invention will be apparent to those skilled in the art. For example, an almost limitless number of different implementations of the computer program that captures and processes images from LB microscopes are possible, with different modular organizations, control structures, data structures, and other programming parameters and written in any of a variety of different programming languages for execution on many different operating-system and hardware platforms. A variety of different components may be used to produce an LB microscope of the present invention. Commercial image multiplexors may be used for multiplexing the captured optical image, or, in other embodiments, a simple four-way prism arrangement may be used to split an input optical image into four sub-images. The image capture and processing may be carried out on a personal computer electronically connected to an enhanced optical microscope or may be carried out by processors and software embedded directly into the instrument. In additional embodiments, the multi-way image multiplexing and analyzing, and subsequent multi-sub-image capture and computational processing can be carried out on images obtained via various different imaging systems, including photographic cameras, optical telescopes, and other such imaging systems, in order to compute and display polarization effects detected by methods of the present invention in the images.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A real-time linear-birefringence-measuring microscope comprising:
    an optical system that produces an image from circularly polarized light passed through a sample;
    a multiplexing analyzer that produces multiple, plane-polarized subimages from the image; and
    an image-capture and image-processing subsystem that captures and processes the multiple, plane-polarized subimages in real time to produce processed images that encode polarization characteristics of the image.

2. The real-time linear-birefringence-measuring microscope of claim 1 wherein the optical system further comprises:
    a light source;
    a polarizer that plane polarizes light emitted by the light source in order to produce plane polarized light;
    a quarter-wave plate that introduces an anisotropic phase change in the plane polarized light emitted by the polarizer in order to produce the circularly polarized light that is passed through the sample; and
    an optical system that produces an image from the circularly polarized light Passed through the sample.

3. The real-time linear-birefringence-measuring microscope of claim 1 wherein the multiplexing analyzer further comprises:
    an image multiplexer that produces multiple subimages from the image produced by the optical system; and
    a multi-way polarizer/analyzer that plane-polarizes each sub-image in a different direction to produce multiple, analyzed subimages.

4. The real-time linear-birefringence-measuring microscope of claim 3
    wherein the image multiplexer produces four subimages from the image produced by the optical system; and
    wherein the multi-way polarizer/analyzer plane-polarizes the four subimages at angular orientations of 0 radians, $\pi/4$ radians, $\pi/2$ radians, and $3\pi/4$ radians with respect to a multi-way polarizer/analyzer reference frame.

5. The real-time linear-birefringence-measuring microscope of claim 1 wherein the image-capture and image-processing subsystem further comprises:
    an electronic detection system that produces an electronic-intensity-data representation of the multiple, analyzed subimages; and
    a processing component that processes the electronic-intensity-data representation Of the multiple, analyzed subimages to produce processed images that encode polarization characteristics of the image originally produced by the optical system.

6. The real-time linear-birefringence-measuring microscope of claim 5 wherein the electronic detection system that produces an electronic-intensity-data representation of the multiple, analyzed subimages further comprises a charge-coupled detector and an image-capture software subsystem that stored the electronic-intensity-data representation of the multiple, analyzed subimages in an electronic-memory buffer.

7. The real-time linear-birefringence-measuring microscope of claim 6 wherein the image-capture and image-processing subsystem further comprises:
a executable software component that processes the electronic-intensity-data representation of the multiple, analyzed subimages stored in the electronic-memory buffer by referencing the stored electronic-intensity-data representation of the multiple, analyzed subimages as a pixel-intensity array to produce processed images that encode polarization characteristics of the image originally produced by the optical system.

8. The real-time linear-birefringence-measuring microscope of claim 7 wherein the multiple, analyzed subimages include:
a first sub-image $I_1$ plane polarized at 0 radians with respect to a polarizer/analyzer reference frame;
a second sub-image $I_2$ plane polarized at $\pi/4$ radians with respect to the polarizer/analyzer reference frame;
a third sub-image $I_3$ plane polarized at $\pi/2$ radians with respect to the polarizer/analyzer reference frame; and
a fourth sub-image $I_4$ plane polarized at $3\pi/4$ radians with respect to the polarizer/analyzer reference frame.

9. The real-time linear-birefringence-measuring microscope of claim 8 wherein intensities for each pixel in the subimages are calculated as:

$$I_i = \frac{I_0}{2}[1 + \sin2(\alpha_i - \phi)\sin\delta]$$

where $I_i$=the intensity for the pixel measured at an angle $\alpha_i$
$I_0$=the intensity of the circularly polarized light input to the region of the sample corresponding to the pixel;
$\alpha_i$=the angle at which the multi-way polarizer/analyzer plane-polarizes light transmitted through the sample in order to measure the intensity $I_i$; and $$\delta = \frac{2\pi d(n_y - n_x)}{\lambda} =$$

the analytic phase difference introduced by the sample where d is the width of the sample, $n_y$ and $n_x$ are indexes of refraction in orthogonal y and x directions, and $\lambda$ is the wavelength of the circularly polarized light.

10. The real-time linear-birefringence-measuring microscope of claim 9
wherein intensities for each pixel in the subimages are alternatively calculated as:

$$I_i = a_0 + a_1\sin2\alpha_i + a_2\cos2\alpha_i$$

where, $$a_0 = \frac{I_0}{2}$$

$$a_1 = \frac{I_0}{2}\cos2\phi\sin\delta$$

$$a_2 = -\frac{I_0}{2}\sin2\phi\sin\delta,$$

and wherein the coefficients $a_0$, $a_1$, and $a_2$ are computed from intensities of pixels In the four subimages as:

$$a_0 = \frac{I_1 + I_2 + I_3 + I_4}{4}$$

$$a_1 = \frac{I_2 - I_4}{2}$$

$$a_2 = \frac{I_1 - I_3}{2}.$$

11. The real-time linear-birefringence-measuring microscope of claim 10
wherein the image-capture and image-processing subsystem computes a birefringence for each pixel in a quarter-sized representation of the image produced by the optical system as:

$$|\sin\delta| = \frac{1}{a_0}\sqrt{a_1^2 + a_2^2}$$

and wherein the image-capture and image-processing subsystem generates and displays a false-color quarter-sized image with the intensity of each pixel in the false-color image proportional to the computed birefringence for the pixel.

12. The real-time linear-birefringence-measuring microscope of claim 11 wherein the computed birefringence for each pixel is numerically, linearly encoded in a color channel of the pixel.

13. The real-time linear-birefringence-measuring microscope of claim 10
wherein the image-capture and image-processing subsystem computes an extinction angle $\phi$ for each pixel in a quarter-sized representation of the image produced by the optical system as:

$$\phi = \frac{\pi}{2} + \text{sign}(a_2)\frac{1}{2}\cos^{-1}\left(\frac{-a_1}{\sqrt{a_1^2 + a_2^2}}\right)$$

and wherein the image-capture and image-processing subsystem generates and displays a false-color quarter-sized image with the intensity of each pixel in the false-color image proportional to the computed extinction angle for the pixel.

14. The real-time linear-birefringence-measuring microscope of claim 13 wherein the computed extinction angle for each pixel is numerically, linearly encoded in a color channel of the pixel.

15. The real-time linear-birefringence-measuring microscope of claim 10
wherein the image-capture and image-processing subsystem computes a transmission for each pixel in a quarter-sized representation of the image produced by the optical system as:

$$a_0$$

and wherein the image-capture and image-processing subsystem generates and displays a false-color quarter-sized image with the intensity of each pixel in the false-color image proportional to the computed transmission for the pixel.

16. The real-time linear-birefringence-measuring microscope of claim 15 wherein the computed transmission for each pixel is numerically, linearly encoded in a color channel of the pixel.

17. A real-time polarization-effects-measuring microscope comprising:
   an optical system that produces an image from light passed through a sample;
   a multiplexing analyzer that produces multiple, plane-polarized subimages from the image; and
   an image-capture and image-processing subsystem that captures and processes the multiple, plane-polarized subimages in real time to produce processed images that encode polarization characteristics of the image.

18. The real-time polarization-effects-measuring microscope of claim 17 wherein the optical system further comprises:
   a light source;
   a polarizer that plane polarizes light emitted by the light source in order to produce plane polarized light; and
   an optical system that produces an image from the plane polarized light passed through the sample.

19. The real-time polarization-effects-measuring microscope of claim 18 wherein the polarization-effects-measuring microscope computes and displays optical activity of a non-birefringent sample.

20. The real-time polarization-effects-measuring microscope of claim 17 wherein the optical system further comprises:
   a light source; and
   an optical system that produces an image from the light passed through the sample.

21. The real-time polarization-effects-measuring microscope of claim 20 wherein the polarization-effects-measuring microscope computes and displays linear dichroism of a sample.

22. The real-time polarization-effects-measuring microscope of claim 17 wherein the optical system further comprises:
   a light source;
   a polarizer that plane polarizes light emitted by the light source in order to produce plane polarized light;
   a short-wavelength etch filter;
   the sample;
   a long-wavelength etch filter; and
   an optical system that produces an image from the plane-polarized light passed through the sample.

23. The real-time polarization-effects-measuring microscope of claim 22 wherein the polarization-effects-measuring microscope computes and displays anisotropic fluorescent emission from a sample.

24. The real-time polarization-effects-measuring microscope of claim 17 wherein the polarization-effects-measuring microscope optical system further comprises:
   a light source;
   a polarizer that plane polarizes light emitted by the light source in order to produce plane polarized light;
   a quarter-wave plate that introduces an anisotropic phase change in the plane polarized light emitted by the polarizer in order to produce the circularly polarized light that is passed through the sample; and
   an optical system that produces an orthoscopic image from the circularly polarized light passed through the sample.

25. The real-time polarization-effects-measuring microscope of claim 24 wherein the polarization-effects-measuring microscope computes and displays linear birefringence of a sample.

26. The real-time polarization-effects-measuring microscope of claim 17 wherein the polarization-effects-measuring microscope optical system further comprises:
   a light source;
   a polarizer that plane polarizes light emitted by the light source in order to produce plane polarized light;
   a quarter-wave plate that introduces an anisotropic phase change in the plane polarized light emitted by the polarizer in order to produce the circularly polarized light that is passed through the sample; and
   an optical system that produces an conoscopic image from the circularly polarized light passed through the sample.

27. The real-time polarization-effects-measuring microscope of claim 26 wherein the computes and displays linear birefringence of a sample.

28. A method for measuring and displaying polarizing effects in a sample, the method comprising:
   producing an image by using an optical system that passes light through a sample;
   producing multiple, plane-polarized subimages from the image using a multiplexing analyzer; and
   capturing and processing the multiple, plane-polarized subimages in real time to produce processed images that encode polarization characteristics of the sample.

29. The method of claim 28
   wherein the optical system further comprises:
      a light source;
      a polarizer that plane polarizes light emitted by the light source in order to produce plane polarized light;
      a quarter-wave plate that introduces an anisotropic phase change in the plane polarized light emitted by the polarizer in order to produce circularly polarized light that is passed through the sample; and
      an optical system that produces an orthoscopic image from the circularly polarized light passed through the sample; and
   wherein linear birefringence is measured and displayed.

30. The method of claim 28
   wherein the optical system further comprises:
      a light source;
      a polarizer that plane polarizes light emitted by the light source in order to produce plane polarized light;
      a quarter-wave plate that introduces an anisotropic phase change in the plane polarized light emitted by the polarizer in order to produce circularly polarized light that is passed through the sample; and
      an optical system that produces a conoscopic image from the circularly polarized light passed through the sample; and
   wherein linear birefringence is measured and displayed.

31. The method of claim 28
   wherein the optical system further comprises:
      a light source;
      a polarizer that plane polarizes light emitted by the light source in order to produce plane polarized light; and
      an optical system that produces an image from the plane polarized light passed through the sample; and
   wherein optical activity of a non-birefringent sample is measured and displayed.

32. The method of claim 28
   wherein the optical system further comprises:
      a light source; and
      an optical system that produces an image from the light passed through the sample; and
   wherein linear dichroism is measured and displayed.

33. The method of claim 28
wherein the optical system further comprises:
a light source;
a polarizer that plane polarizes light emitted by the light source in order to produce plane polarized light;
a short-wavelength etch filter;
the sample;
a long-wavelength etch filter; and
an optical system that produces an image from the plane-polarized light passed through the sample; and
wherein anisotropic fluorescent emission is measured and displayed.

34. The method of claim 28 wherein the multiplexing analyzer further comprises:
an image multiplexer that produces multiple subimages from the image produced by the optical system; and
a multi-way polarizer/analyzer that plane-polarizes each sub-image in a different direction to produce multiple, analyzed subimages.

35. The method of claim 34 wherein producing multiple, plane-polarized subimages from the image further comprises:
producing four subimages from the image using the image multiplexer; and
plane-polarizing the four subimages at angular orientations of 0 radians, π/4 radians, π/2 radians, and 3π/4 radians with respect to a multi-way polarizer/analyzer reference frame using the multi-way polarizer/analyzer.

36. The method of claim 28 wherein the image-capture and image-processing subsystem further comprises:
an electronic detection system that produces an electronic-intensity-data representation of the multiple, analyzed subimages; and
a processing component that processes the electronic-intensity-data representation of the multiple, analyzed subimages to produce images that encode polarization characteristics of the image originally produced by the optical system.

37. The method of claim 28 wherein the electronic detection system that produces an electronic-intensity-data representation of the multiple, analyzed subimages further comprises a charge-coupled detector and an image-capture software subsystem that stored the electronic-intensity-data representation of the multiple, analyzed subimages in an electronic-memory buffer.

38. The method of claim 37 wherein processing the multiple, plane-polarized subimages in real time to produce images that encode polarization characteristics of the sample further comprises:
processing the electronic-intensity-data representation of the multiple, analyzed subimages stored in the electronic-memory buffer by referencing the stored electronic-intensity-data representation of the multiple, analyzed subimages as a pixel-intensity array to produce images that encode polarization characteristics of the image originally produced by the optical system.

39. The method of claim 38 wherein the multiple, analyzed subimages include:
a first sub-image $I_1$ plane polarized at 0 radians with respect to a polarizer/analyzer reference frame;
a second sub-image $I_2$ plane polarized at π/4 radians with respect to the polarizer/analyzer reference frame;
a third sub-image $I_3$ plane polarized at π/2 radians with respect to the polarizer/analyzer reference frame; and
a fourth sub-image $I_4$ plane polarized at 3π/4 radians with respect to the polarizer/analyzer reference frame.

40. The method of claim 39 further comprising computing intensities for each pixel in the subimages as:

$$I_i = \frac{I_0}{2}[1 + \sin2(\alpha_i - \phi)\sin\delta]$$

where $I_i$=the intensity for the pixel measured at an angle $\alpha_i$
$I_0$=the intensity of the circularly polarized light input to the region of the sample corresponding to the pixel;
$\alpha_i$=the angle at which the multi-way polarizer/analyzer plane-polarizes light transmitted through the sample in order to measure the intensity $I_i$; and $$\delta = \frac{2\pi d(n_y - n_x)}{\lambda} =$$

the analytic phase difference introduced by the sample where d is the width of the sample, $n_y$ and $n_x$ are indexes of refraction in orthogonal y and x directions, and λ is the wavelength of the circularly polarized light.

41. The method of claim 40 further comprising computing intensities for each pixel in the subimages as:

$$I_i = a_0 + a_1\sin2\alpha_i + a_2\cos2\alpha_i$$

wherein, $$a_0 = \frac{I_0}{2}$$

$$a_1 = \frac{I_0}{2}\cos2\phi\sin\delta$$

$$a_2 = -\frac{I_0}{2}\sin2\phi\sin\delta,$$

and wherein the coefficients $a_0$, $a_1$, and $a_2$ are computed from intensities of pixels in the four subimages as:

$$a_0 = \frac{I_1 + I_2 + I_3 + I_4}{4}$$

$$a_1 = \frac{I_2 - I_4}{2}$$

$$a_2 = \frac{I_1 - I_3}{2}.$$

42. The method of claim 41 further comprising:
computing a birefringence for each pixel in a quarter-sized representation of the image as:

$$|\sin\delta| = \frac{1}{a_0}\sqrt{a_1^2 + a_2^2}$$

and generating and displaying a false-color quarter-sized image with the intensity Of each pixel in the false-color image proportional to the computed birefringence for the pixel.

43. The method of claim 41 further comprising:
computing an extinction angle φ for each pixel in a quarter-sized representation of the image produced by the optical system as:

$$\phi = \frac{\pi}{2} + \text{sign}(a_2)\frac{1}{2}\cos^{-1}\left(\frac{-a_1}{\sqrt{a_1^2 + a_2^2}}\right)$$

and generating and displaying a false-color quarter-sized image with the intensity of each pixel in the false-color image proportional to the computed extinction angle for the pixel.

44. The method of claim 41 further comprising:
computing a transmission for each pixel in a quarter-sized representation of the image produced by the optical system as:

$a_0$ and generating and displaying a false-color quarter-sized image with the intensity of each pixel in the false-color image proportional to the computed transmission for the pixel.

45. A real-time polarization-effects-measuring image-capture and image-processing system, the system comprising:
an optical subsystem that produces an image from light passed through a sample;
a multiplexing analyzer that produces multiple, plane-polarized subimages from the image; and
an image-capture and image-processing subsystem that captures and processes the multiple, plane-polarized subimages in real time to produce processed images that encode polarization characteristics of the image.

* * * * *